(12) United States Patent
Adin et al.

(10) Patent No.: US 10,280,173 B2
(45) Date of Patent: May 7, 2019

(54) IBRUTINIB SOLID FORMS AND PRODUCTION PROCESS THEREFOR

(71) Applicant: WAVELENGTH ENTERPRISES LTD., Bnei Brak (IL)

(72) Inventors: Itai Adin, Beer Sheva (IL); Sonia Krivonos, Beer Sheva (IL); Yevgeny Rozenblat, Beer Sheva (IL); Alex Weisman, Kyriat Ekron (IL); Ana Fernandez Casares, Amsterdam (NL); Gloria Ten Figas, Amsterdam (NL); Revital Ben-Daniel, Modiin (IL)

(73) Assignee: WAVELENGTH ENTERPRISES LTD, Bnei Brak (IL)

( * ) Notice: Subject to any disclaimer, the term of this patent is extended or adjusted under 35 U.S.C. 154(b) by 0 days.

(21) Appl. No.: 15/853,368

(22) Filed: Dec. 22, 2017

(65) Prior Publication Data
US 2018/0251463 A1 Sep. 6, 2018

Related U.S. Application Data

(62) Division of application No. 15/128,856, filed as application No. PCT/IL2015/000017 on Mar. 23, 2015, now Pat. No. 9,884,869.

(60) Provisional application No. 62/045,869, filed on Sep. 4, 2014, provisional application No. 61/971,164, filed on Mar. 27, 2014.

(51) Int. Cl.
*A61K 31/519* (2006.01)
*C07D 487/04* (2006.01)
(52) U.S. Cl.
CPC .......... *C07D 487/04* (2013.01); *A61K 31/519* (2013.01); *C07B 2200/13* (2013.01)

(58) Field of Classification Search
CPC .......................... A61K 31/519; C07D 487/04
USPC ....................................... 514/262.1; 544/262
See application file for complete search history.

(56) References Cited

U.S. PATENT DOCUMENTS

| | | |
|---|---|---|
| 2013/0041014 A1 | 2/2013 | Lavitrano et al. |
| 2013/0338172 A1 | 12/2013 | Smyth et al. |
| 2014/0079690 A1 | 3/2014 | Buggy et al. |

FOREIGN PATENT DOCUMENTS

| | | |
|---|---|---|
| CN | 103694241 A | 4/2014 |
| WO | WO 2013/184572 A1 | 12/2013 |
| WO | WO 2014/004707 A1 | 1/2014 |

OTHER PUBLICATIONS

U.S. Appl. No. 15/128,856, filed Sep. 23, 2016.
United States Patent and Trademark Office, International Search Report in International Application No. PCT/IL2015/000017 (dated Sep. 24, 2015).
United States Patent and Trademark Office, Written Opinion in International Application No. PCT/IL2015/000017 (dated Sep. 24, 2015).
International Bureau of WIPO, International Preliminary Report on Patentability in International Application No. PCT/IL2015/000017 (dated Sep. 24, 2015).

*Primary Examiner* — Jeffrey H Murray
(74) *Attorney, Agent, or Firm* — Leydig, Voit & Mayer, Ltd.

(57) ABSTRACT

Provided are ibrutinib polymorphs, e.g., crystalline ibrutinib Forms III, IV, V, VI, VII, VIII and Form IX and processes for producing these crystalline forms, stable amorphous ibrutinib and processes for preparing stable amorphous ibrutinib, pharmaceutical compositions comprising these forms and methods of using these crystalline and amorphous forms.

13 Claims, 24 Drawing Sheets

IBRUTINIB SOLID FORMS AND PRODUCTION PROCESS THEREFOR

CROSS-REFERENCE TO RELATED APPLICATIONS

This patent application is a divisional of co-pending U.S. patent application Ser. No. 15/128,856, filed Sep. 23, 2016, which is the U.S. national phase of International Application No. PCT/IL2015/000017, filed on Mar. 23, 2015, which claims the benefit of U.S. Provisional Application No. 61/971,164, filed Mar. 27, 2014, and U.S. Provisional Application No. 62/045,869, filed Sep. 4, 2014, the disclosures of which are incorporated herein by reference in their entireties for all purposes.

BACKGROUND OF THE INVENTION

Ibrutinib (IMBRUVICA™) is an orally administered drug that targets Bruton's tyrosine kinase (Btk). Btk is a member of the Tec tyrosine kinase family, which is expressed in most hematopoietic cells such as B cells. Btk plays a role in the development and activation of B cells. Mutations in the human Bkt gene cause the inherited disease X-linked agammaglobulinemia (XLA), with lack of peripheral B cells and low levels of serum Ig. In XLA, the primary immune deficit is B cell specific. Ibrutinib may be used for treating both B cell-related hematological cancers such as non-Hodgkin lymphoma and B cell chronic lymphocytic leukemia, and autoimmune diseases such as rheumatoid arthritis, Sjogrens syndrome, lupus and asthma.

The chemical name of ibrutinib is 1-[(3R)-3-[4-amino-3-(4-phenoxyphenyl)-1H-pyrazolo[3,4-d]pyrimidin-1-yl]piperidin-1-yl]prop-2-en-1-one and it has the following chemical formula:

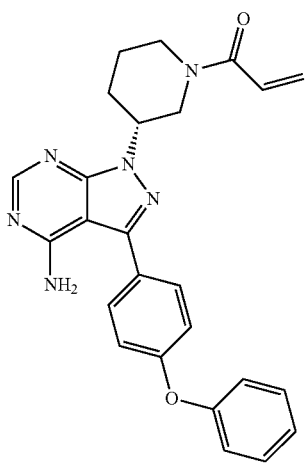 [SMILES: C=CC(=O)N1CCC[C@@H](n2nc(-c3ccc(Oc4ccccc4)cc3)c3c(N)ncnc32)C1]

According to the Patient Leaflet of IMBRUVICA™, the drug's capsules for oral administration are supplied as white opaque capsules containing 140 mg ibrutinib as active pharmaceutical ingredient and excipients. The proposed dosing regimen of IMBRUVICA™ capsules is 560 mg (4×140 mg) once daily of ibrutinib to patients with Mantle Cell Lymphoma (MCL) or chronic lymphocytic leukemia (CLL).

International Patent Publication Number WO2013/184572 discloses crystalline forms including solvates of ibrutinib that are marked as Forms A, B, C, D, E and F. Also disclosed in Publication WO2013/184572 are pharmaceutical compositions that include ibrutinib, as well as methods of using it, alone or in combination with other therapeutic agents, for the treatment of autoimmune diseases or conditions, heteroimmune diseases or conditions, cancer, including lymphoma, and inflammatory diseases or conditions.

The preparation of ibrutinib Form A is described in Routes 1-3 of example 1 of WO2013/184572. According to Route 1, an amorphous ibrutinib is dissolved or slurried in an organic solvent such as methyl tert-butyl ether or diisopropyl ether, or in a 10% aqueous mixture of an organic solvent such as acetone or isopropyl alcohol. The mixture is heated to 50° C. for one hour and then cooled to afford crystallization. According to Route 2, amorphous ibrutinib is mixed with water or with an aqueous mixture of isopropanol or with an organic solvent such as dioxane, toluene or anisole. Then, a sealed vial is placed in a maturation chamber cycling between 50° C. and ambient temperature for four hours each for five days to afford formation of solids. According to Route 3, ibrutinib is dissolved in methanol at 45° C. and water is added to form slurry, which is stirred at the elevated temperature for 3 hours. Then, the slurry is allowed to cool to ambient temperature and stirred for 16 hours followed by filtration to afford a solid. The solid is washed with a mixture of methanol and water and dried.

Application CN103694241 describes a new crystalline form of ibrutinib, which is denoted therein as "Form A". The TGA presented in application CN103694241 may suggest that this form is a solvate of ibrutinib.

Ibrutinib is administered orally (560 mg/daily) to patients in order to obtain the desired therapeutic effect. The need for such a high dose of ibrutinib may be related to low bioavailability (the oral bioavailability of ibrutinib is reported to be 22.8% in rats) and in turn may be related to the adverse effects associated with the use of ibrutinib such as nausea or emesis, dizziness and diarrhea. Low bioavailability may be also related to variable absorption and potential variability of the desired therapeutic response.

There is a need for stable ibrutinib forms, which may be more soluble, and for processes for preparing such forms. The present invention provides such forms and processes for their preparation.

SUMMARY OF THE INVENTION

The present invention provides crystalline ibrutinib forms that are named herein crystalline ibrutinib Form III, crystalline ibrutinib Form IV, crystalline ibrutinib Form V, crystalline ibrutinib Form VI crystalline Form VII, crystalline ibrutinib Form VIII and crystalline ibrutinib Form IX, as well as processes for obtaining these forms. Also provided by the present invention are stable amorphous ibrutinib forms and processes for obtaining such forms. The present invention provides pharmaceutical compositions comprising at least one of the forms of ibrutinib of the present invention, methods for preparing said compositions as well as methods for using the forms of the present invention and the pharmaceutical compositions in the treatment of diseases or conditions including diseases or conditions for which ibrutinib provides therapeutic benefit to a mammal having the disease or condition such as Mantle Cell Lymphoma (MCL) and Chronic Lymphocytic Leukemia (CLL).

The X-ray powder diffraction patterns, infrared spectra, Raman spectra, and DSC curves for each form are presented in the figures and tables below.

The present invention provides pharmaceutical compositions comprising at least one of the crystalline forms of ibrutinib of the present invention, e.g., Form VII or Form VIII and pharmaceutically acceptable excipients.

The present invention also provides a process for preparing the pharmaceutical compositions comprising at least one of the crystalline forms of ibrutinib of the present invention by mixing said crystalline ibrutinib with pharmaceutically acceptable excipients.

Pharmaceutical compositions of the present invention can comprise, in addition to the crystalline or amorphous forms of ibrutinib of the present invention, other active ingredients. In addition, pharmaceutical compositions of the present invention can comprise inactive ingredients such as absorption accelerators, binders, bulking agents, carriers, diluents, disintegrants, fillers, lubricants, surface-active agents, wetting agents and the like.

The present invention further provides methods of using the ibrutinib forms of the present invention, such as crystalline Form VII, crystalline Form VIII or amorphous ibrutinib in the treatment of diseases or conditions including diseases or conditions for which ibrutinib provides therapeutic benefit to a mammal having the disease or condition, such as, Mantle Cell Lymphoma (MCL) and Chronic Lymphocytic Leukemia (CLL) by administering to a subject in need thereof a therapeutically effective amount of ibrutinib in one or more of the forms of the present invention.

In some embodiments, the present invention provides processes for preparing the crystalline ibrutinib Form III, crystalline ibrutinib Form IV, crystalline ibrutinib Form V, crystalline ibrutinib Form VI, crystalline ibrutinib Form VII, crystalline ibrutinib Form VIII, crystalline ibrutinib Form IX and amorphous ibrutinib. The processes of the present invention for preparing ibrutinib Form III, Form IV, Form V, Form VI, Form VII, Form VIII and Form IX are selected from crystallization, slurrying in a solvent, vapor diffusion onto solids (VDS), vapor diffusion into solutions (VDL), thermal cycling (TCP), drying, exposing the material to accelerated aging conditions (AAC), grinding and combination of said methods.

Several processes for obtaining the crystalline and amorphous forms of the present invention are provided. One process of the present invention for preparing the crystalline ibrutinib Form VII comprises:

dissolving or slurrying ibrutinib in anisole or a mixture of anisole with an additional solvent or an anti-solvent; optionally heating;

optionally adding an anti-solvent;

optionally cooling;

optionally seeding with crystalline ibrutinib Form VII; and isolating the solid and, optionally, drying the solid.

One process of the present invention for preparing the crystalline ibrutinib Form VIII comprise:

dissolving or slurrying ibrutinib in chlorobenzene or a mixture of chlorobenzene with another solvent or anti-solvent;

optionally heating;

optionally adding an anti-solvent;

optionally cooling;

optionally seeding with crystalline ibrutinib Form VIII; and isolating the solid and, optionally, drying the solid.

Also provided by the present invention are stable amorphous ibrutinib forms and processes for obtaining such forms.

One process for obtaining stable amorphous ibrutinib comprises spray drying of ibrutinib, another process comprises milling ibrutinib in a ball-mill, and yet another process comprises freeze-drying of ibrutinib.

In one embodiment the present invention provides a stable amorphous ibrutinb form having slight hygroscopicity. In another embodiment the present invention provides a process for obtaining a stable amorphous ibrutinb form having slight hygroscopicity comprising spray-drying.

The present invention provides pharmaceutical compositions comprising at least one of the crystalline forms of ibrutinib of the present invention, or at least one of the amorphous forms of ibrutinib of the present invention and at least one pharmaceutically acceptable excipient.

The present invention further provides methods of using the crystalline ibrutinib forms or amorphous ibrutinib forms of the present invention, as well as their pharmaceutical compositions in the treatment of diseases or conditions including diseases or conditions for which ibrutinib provides therapeutic benefit to a mammal having the disease or condition, such as, Mantle Cell Lymphoma (MCL) and Chronic Lymphocytic Leukemia (CLL) by administering to a subject in need thereof a therapeutically effective amount of at least one of said ibrutinib forms.

DETAILED DESCRIPTION OF THE INVENTION

The inventors of the present invention have surprisingly discovered new crystalline forms of ibrutinib. One embodiment of the present invention is a new form named herein Form VII. Another embodiment of the present invention is a new form named herein Form VIII.

The present invention additionally provides processes for preparing the crystalline ibrutinib Form VII or Form VIII. The starting material in these processes can be produced by any suitable method, including synthesis methods known in the art. For example, the ibrutinib starting material is obtained as described in Routes 1-3 of Example 1 of International Patent Publication No. WO2013/184572, entitled "Crystalline forms of a Bruton's tyrosine kinase inhibitor".

The processes of the present invention can produce high purity crystalline ibrutinib form VII or Form VIII.

Figure 1:
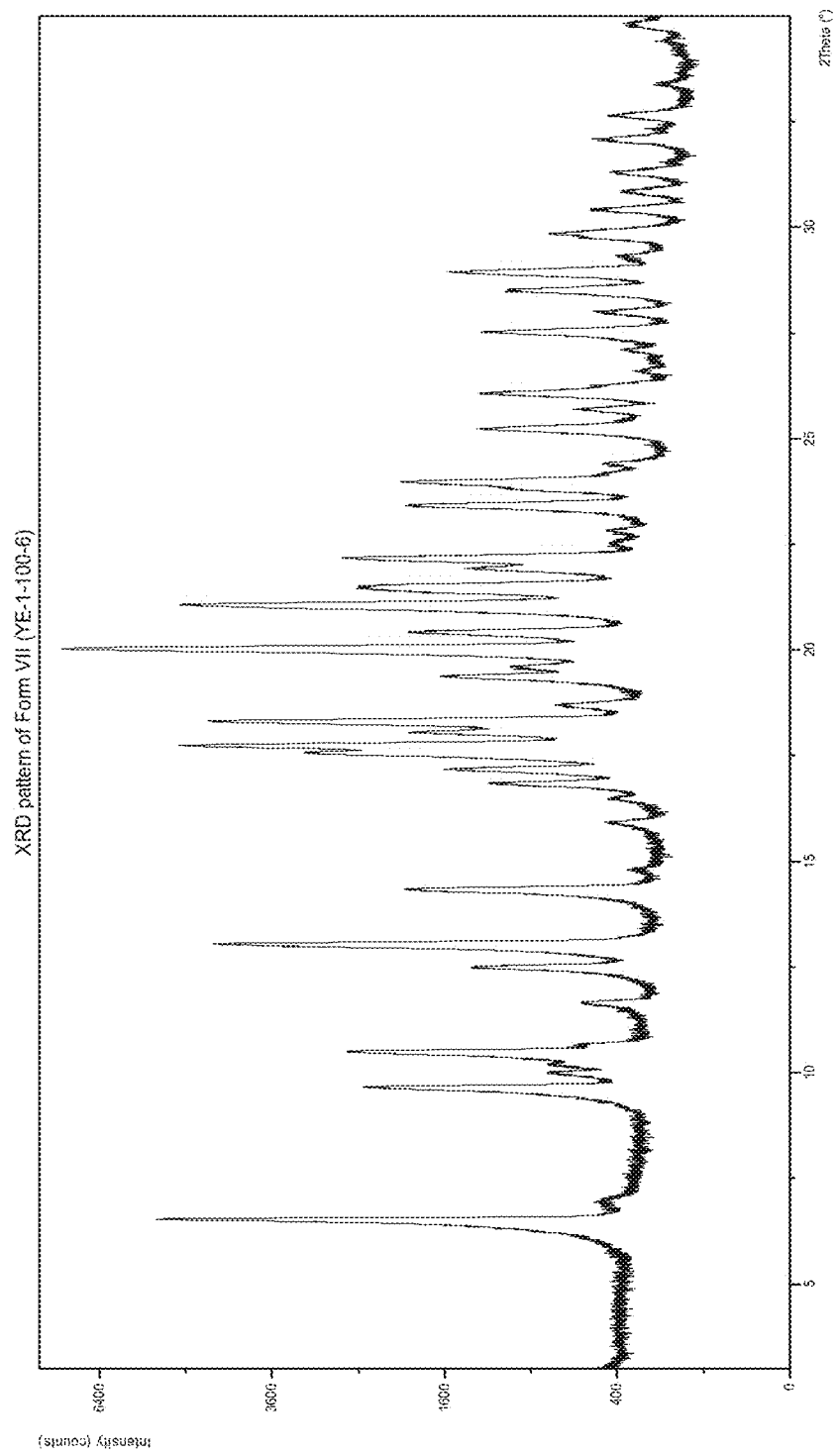
FIG. 1 depicts the X-ray powder diffraction pattern of crystalline ibrutinib Form VII.

The X-ray powder diffraction pattern corresponding to ibrutinib crystalline Form VII is depicted in FIG. 1 and Table 1. The strong diffraction peaks at 6.5, 13.0, 17.7, 18.3, 20.0, 21.0, 21.5, and 23.9±0.2 degrees 2θ are most characteristic of this form. The X-ray powder diffraction peak positions and intensities exhibited by crystalline ibrutinib Form VII are listed in Table 1.

TABLE 1

| No. | Position [°2θ] | Relative Intensity [%] | d-spacing [Å] |
| --- | --- | --- | --- |
| 1 | 6.5 | 50 | 13.63784 |
| 2 | 9.6 | 28 | 9.20001 |
| 3 | 10.5 | 32 | 8.45591 |
| 4 | 11.6 | 3 | 7.60043 |
| 5 | 13.0 | 44 | 6.79535 |
| 6 | 14.3 | 19 | 6.1811 |
| 7 | 15.9 | 3 | 5.57861 |
| 8 | 16.8 | 11 | 5.26564 |
| 9 | 17.2 | 14 | 5.16606 |
| 10 | 17.7 | 83 | 5.01858 |
| 11 | 18.3 | 48 | 4.84628 |
| 12 | 18.7 | 5 | 4.7474 |
| 13 | 19.4 | 21 | 4.58313 |
| 14 | 20.0 | 100 | 4.43859 |
| 15 | 20.4 | 19 | 4.34971 |
| 16 | 21.0 | 64 | 4.21833 |
| 17 | 21.5 | 44 | 4.13612 |
| 18 | 22.1 | 26 | 4.01448 |
| 19 | 23.4 | 21 | 3.79902 |
| 20 | 23.9 | 35 | 3.71785 |
| 21 | 25.2 | 12 | 3.52939 |
| 22 | 26.0 | 13 | 3.41803 |
| 23 | 27.5 | 12 | 3.2403 |
| 24 | 28.5 | 11 | 3.13061 |
| 25 | 28.9 | 16 | 3.08532 |
| 26 | 29.8 | 11 | 2.9933 |
| 27 | 30.4 | 4 | 2.93811 |
| 28 | 30.8 | 3 | 2.89966 |
| 29 | 31.3 | 4 | 2.85933 |
| 30 | 32.1 | 4 | 2.79003 |
| 31 | 32.6 | 3 | 2.7428 |

Figure 2:
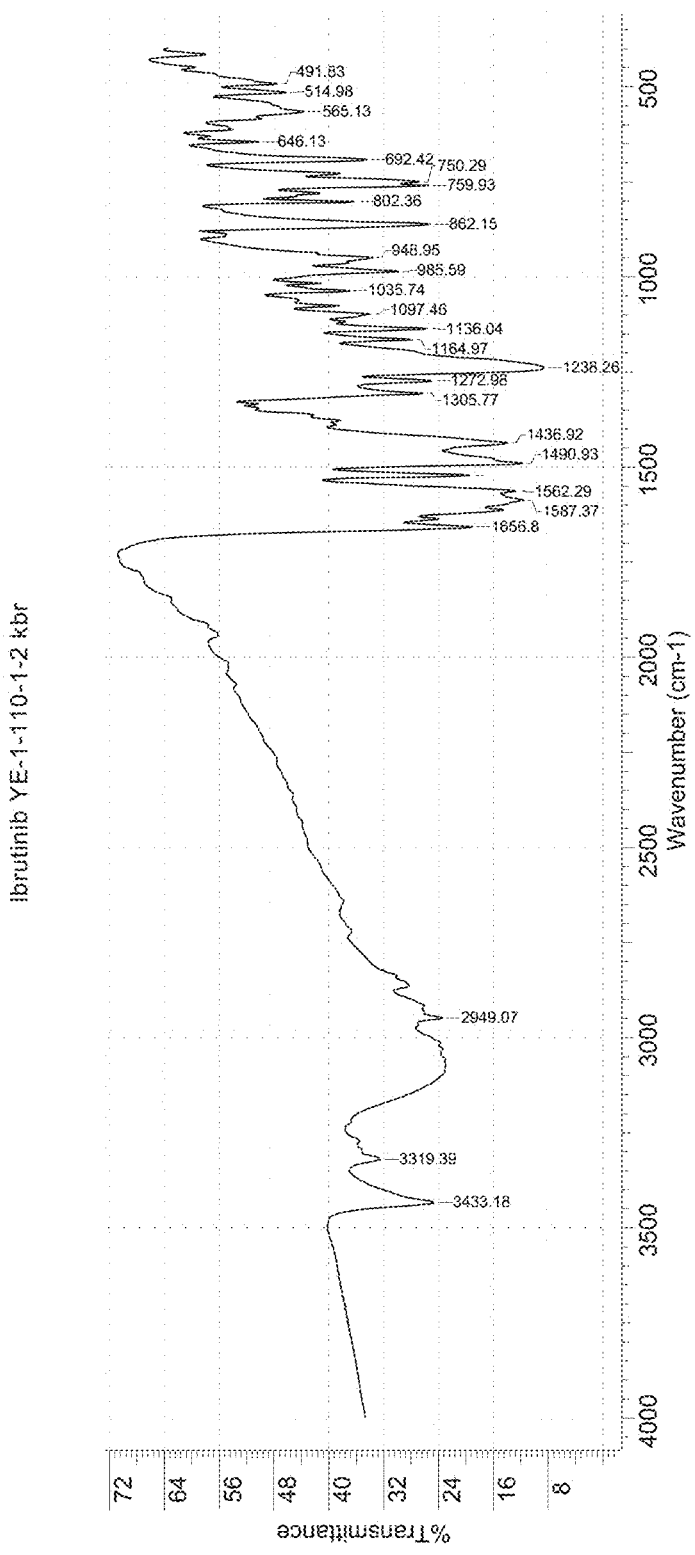
FIG. 2 depicts the infrared spectrum of crystalline ibrutinib Form VII.

An infrared spectrum corresponding to ibrutinib Form VII is depicted in FIG. 2. It has characteristic absorption bands at 3433, 1587, 1491, 1437, 1238, 986, 862, and 692 cm$^{-1}$.

Figure 3:
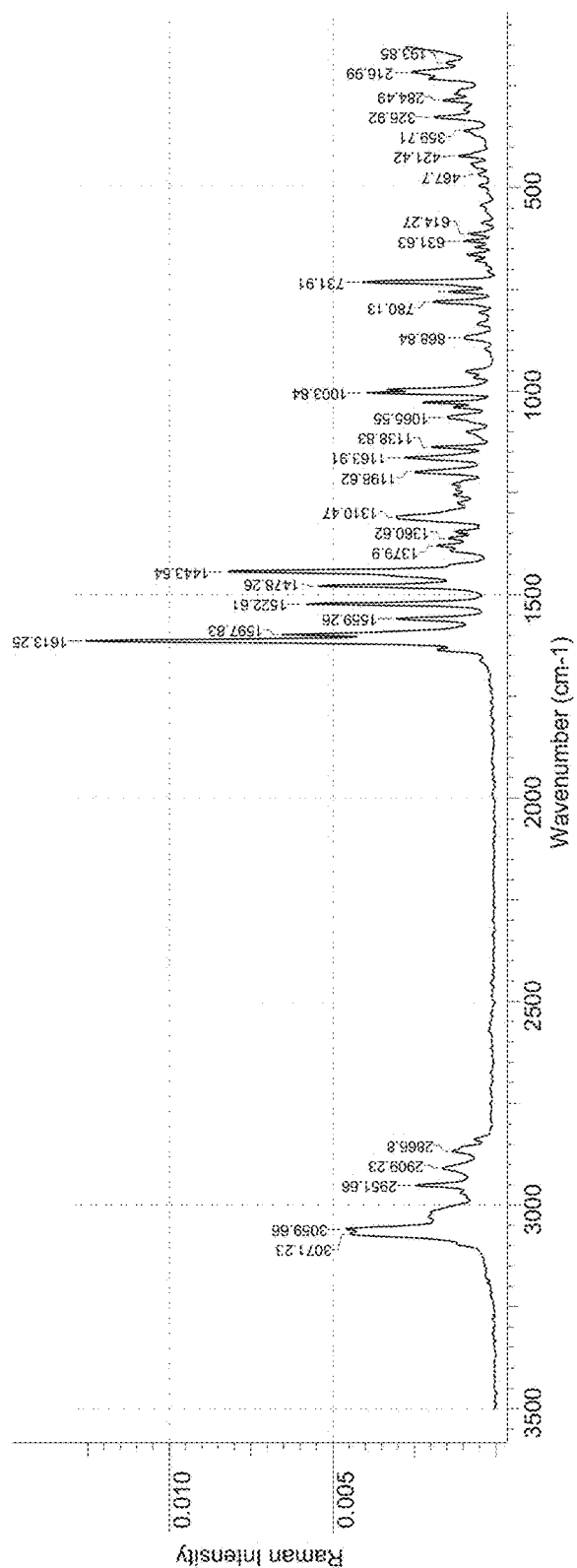
FIG. 3 depicts the Raman spectrum of crystalline ibrutinib Form VII.

The Raman spectrum of crystalline ibrutinib Form VII is depicted in FIG. 3.

Figure 4:
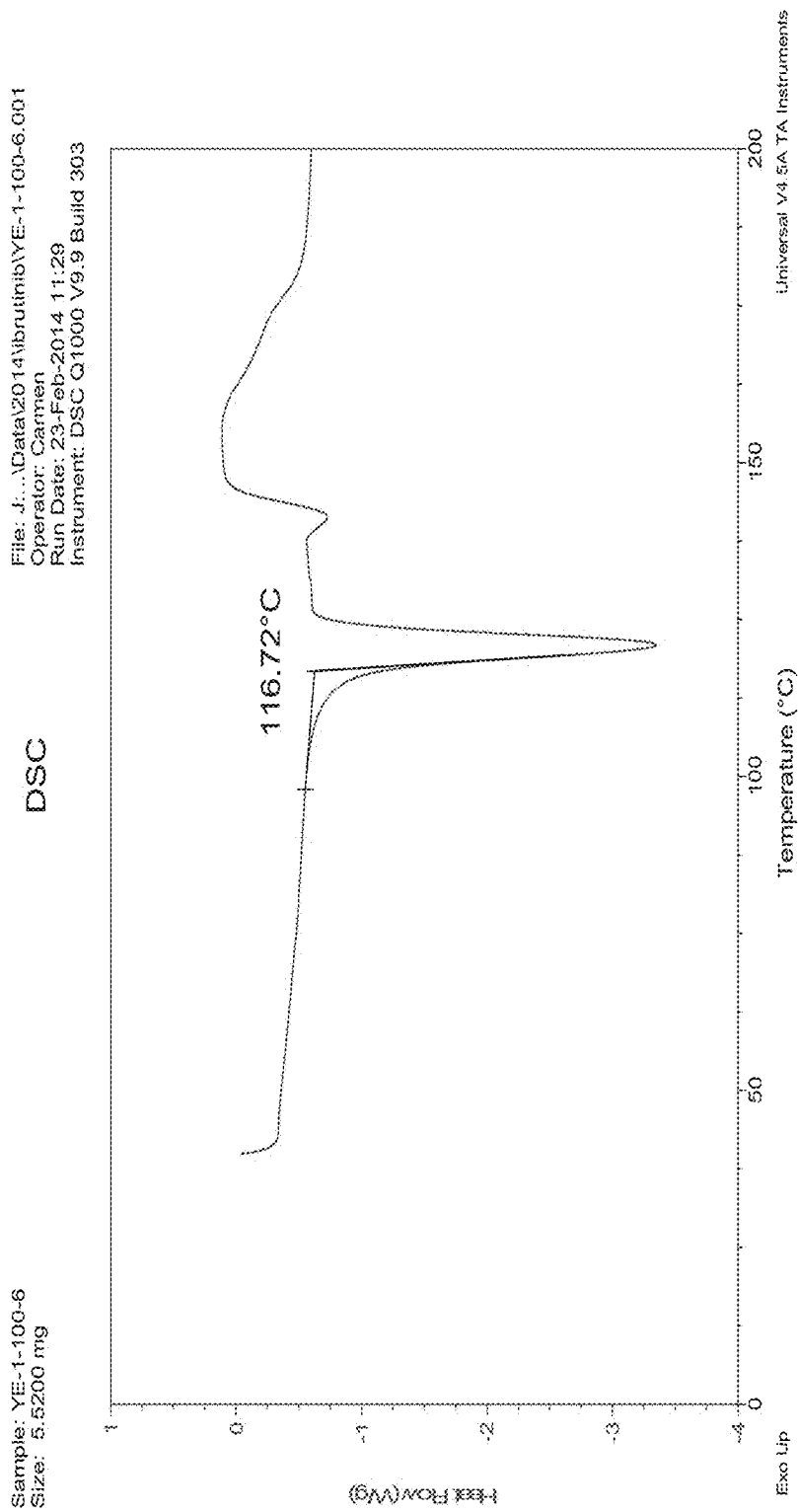
FIG. 4 depicts the DSC curve of crystalline ibrutinib Form VII.

The DSC curve for crystalline ibrutinib Form VII is depicted in FIG. 4 exhibiting peak onset at 116.7° C.

Figure 5:
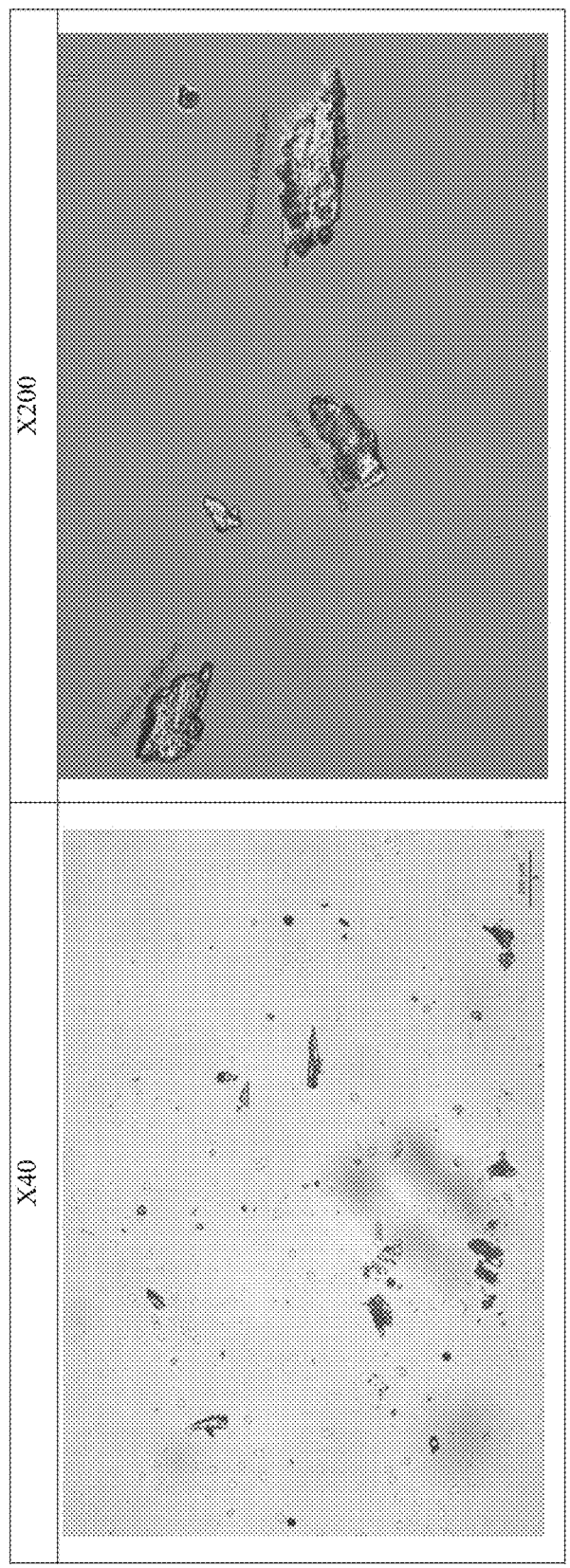
FIG. 5 depicts the optical microscope pictures of crystalline ibrutinib Form VII.

FIG. 5 shows optical microscope pictures of a sample of ibrutinib corresponding to Form VII.

In one embodiment of the present invention ibrutinib form VII is an anisole solvate.

Figure 6:
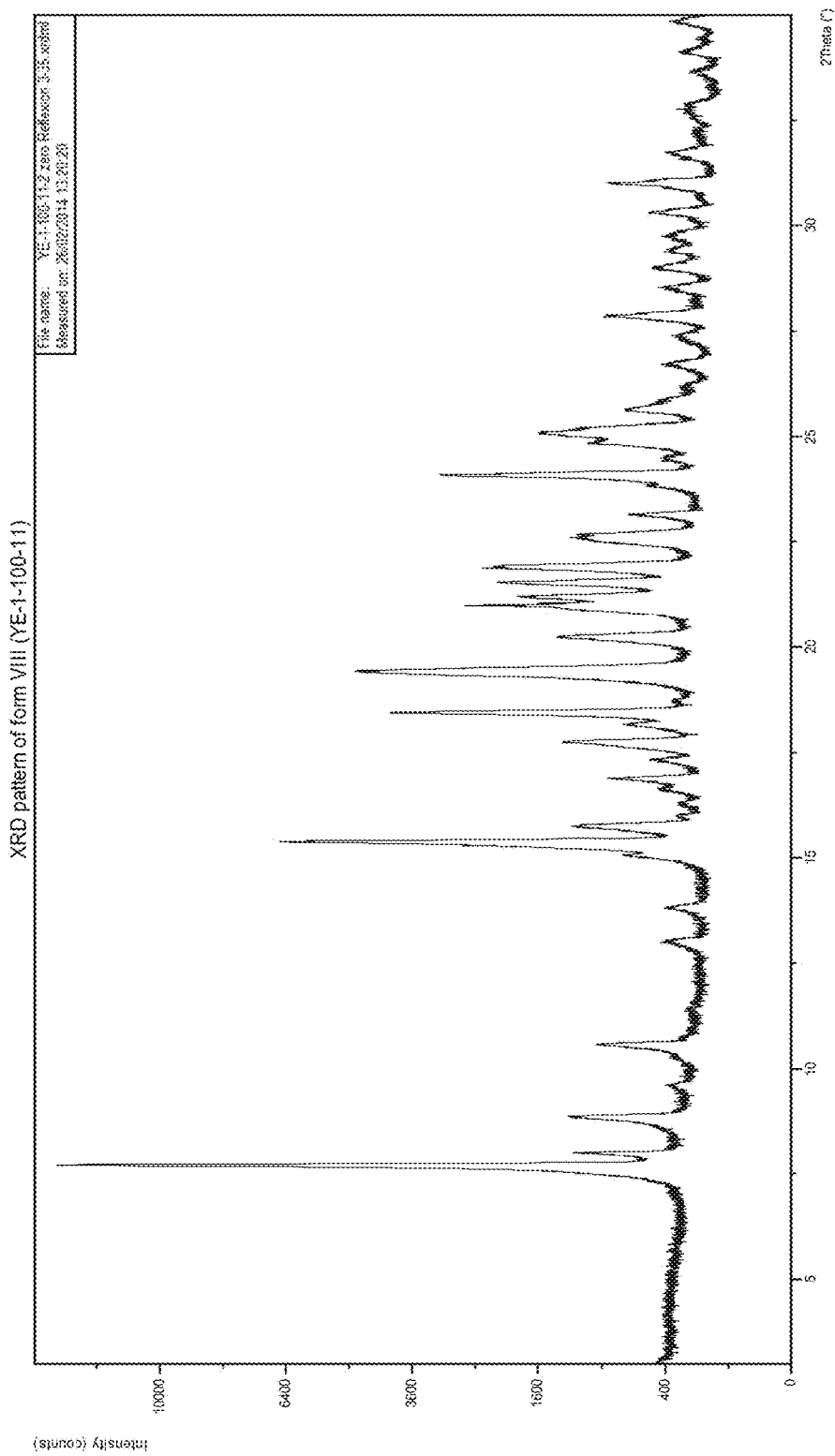
FIG. 6 depicts the X-ray powder diffraction pattern of crystalline ibrutinib Form VIII

The X-ray powder diffraction pattern corresponding to ibrutinib crystalline Form VIII is depicted in FIG. 6 and Table 2. The strong diffraction peaks at 7.7, 15.3, 19.4 and 24.0±0.2 degrees 2θ are most characteristic of this form. The X-ray powder diffraction peak positions and intensities exhibited by crystalline ibrutinib Form VIII are listed in Table 2.

TABLE 2

| No. | Position [°2θ] | Relative Intensity [%] | d-spacing [Å] |
| --- | --- | --- | --- |
| 1 | 7.7 | 100 | 11.52911 |
| 2 | 8.8 | 13 | 10.01107 |
| 3 | 10.5 | 5 | 8.40579 |
| 4 | 13.0 | 4 | 6.80848 |
| 5 | 13.8 | 2 | 6.4216 |
| 6 | 15.3 | 73 | 5.77672 |
| 7 | 15.7 | 8 | 5.62353 |
| 8 | 16.8 | 5 | 5.26301 |
| 9 | 17.7 | 14 | 5.00544 |
| 10 | 18.4 | 16 | 4.81217 |
| 11 | 19.4 | 46 | 4.56892 |
| 12 | 20.2 | 12 | 4.38938 |
| 13 | 20.9 | 14 | 4.23719 |
| 14 | 21.5 | 11 | 4.12835 |
| 15 | 21.9 | 15 | 4.05849 |
| 16 | 22.5 | 12 | 3.94148 |
| 17 | 24.0 | 20 | 3.70241 |
| 18 | 25.1 | 14 | 3.55164 |
| 19 | 25.6 | 10 | 3.47032 |
| 20 | 26.7 | 2 | 3.3388 |
| 21 | 27.3 | 2 | 3.25978 |
| 22 | 27.8 | 4 | 3.20338 |
| 23 | 28.5 | 3 | 3.12922 |
| 24 | 29.0 | 3 | 3.0773 |
| 25 | 30.9 | 8 | 2.88774 |
| 26 | 31.7 | 2 | 2.82129 |
| 27 | 32.7 | 2 | 2.73278 |
| 28 | 34.1 | 1 | 2.62621 |

Figure 7:
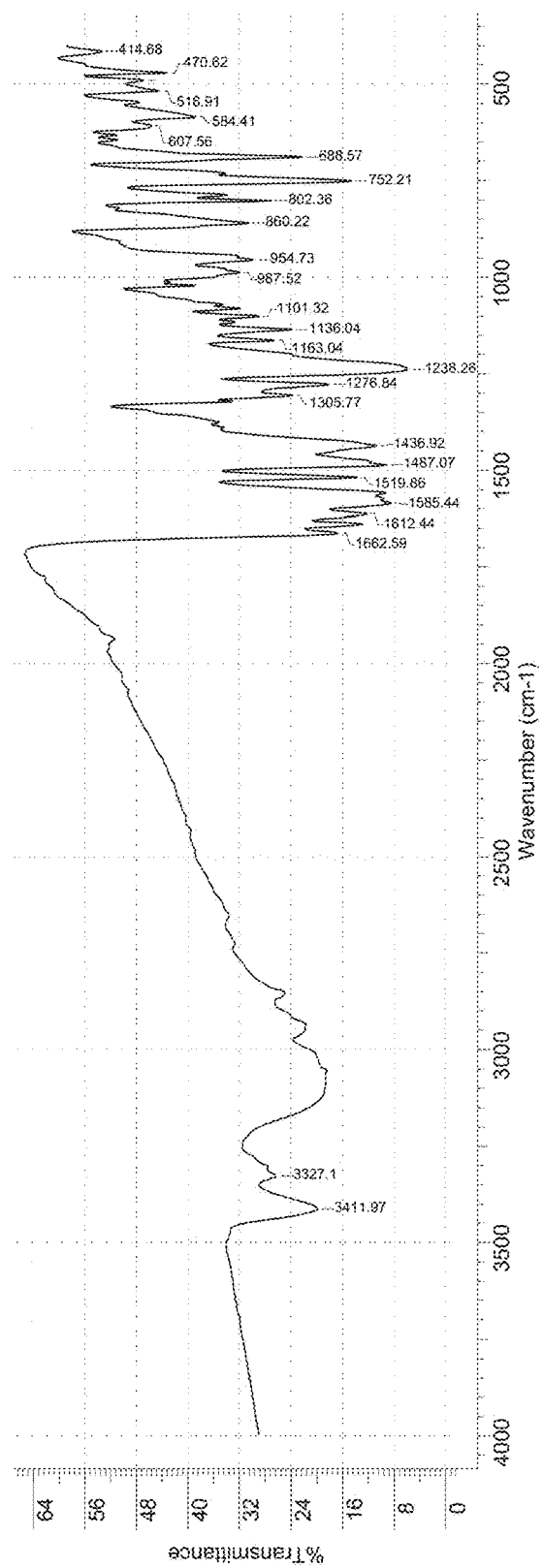
FIG. 7 depicts the Infra-Red spectrum of crystalline ibrutinib Form VIII.

The infrared spectrum of crystalline ibrutinib Form VIII is depicted in FIG. 7. It exhibits characteristic absorption bands at 3412, 1585, 1487, 1437, 1238, 988, 860, 752 and 689 cm$^{-1}$.

Figure 8:
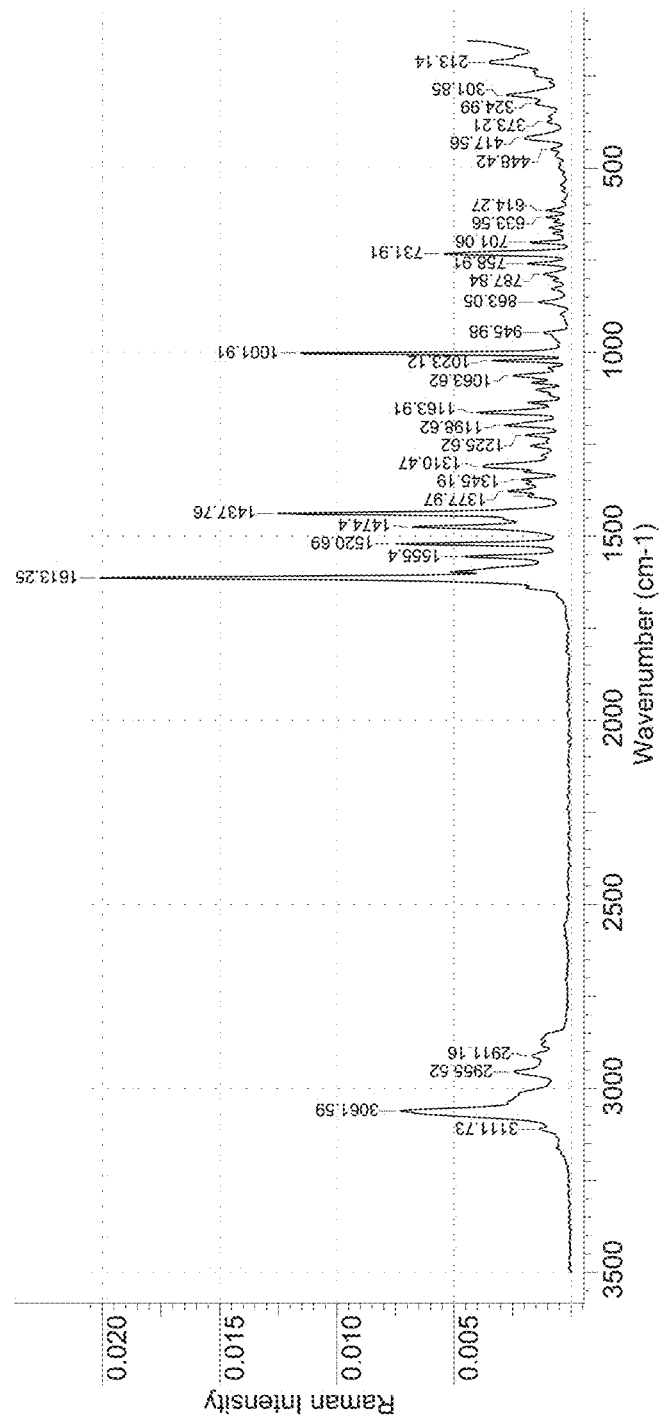
FIG. 8 depicts the Raman spectrum of crystalline ibrutinib Form VIII.

The Raman spectrum of crystalline ibrutinib Form VIII is depicted in FIG. 8.

Figure 9:
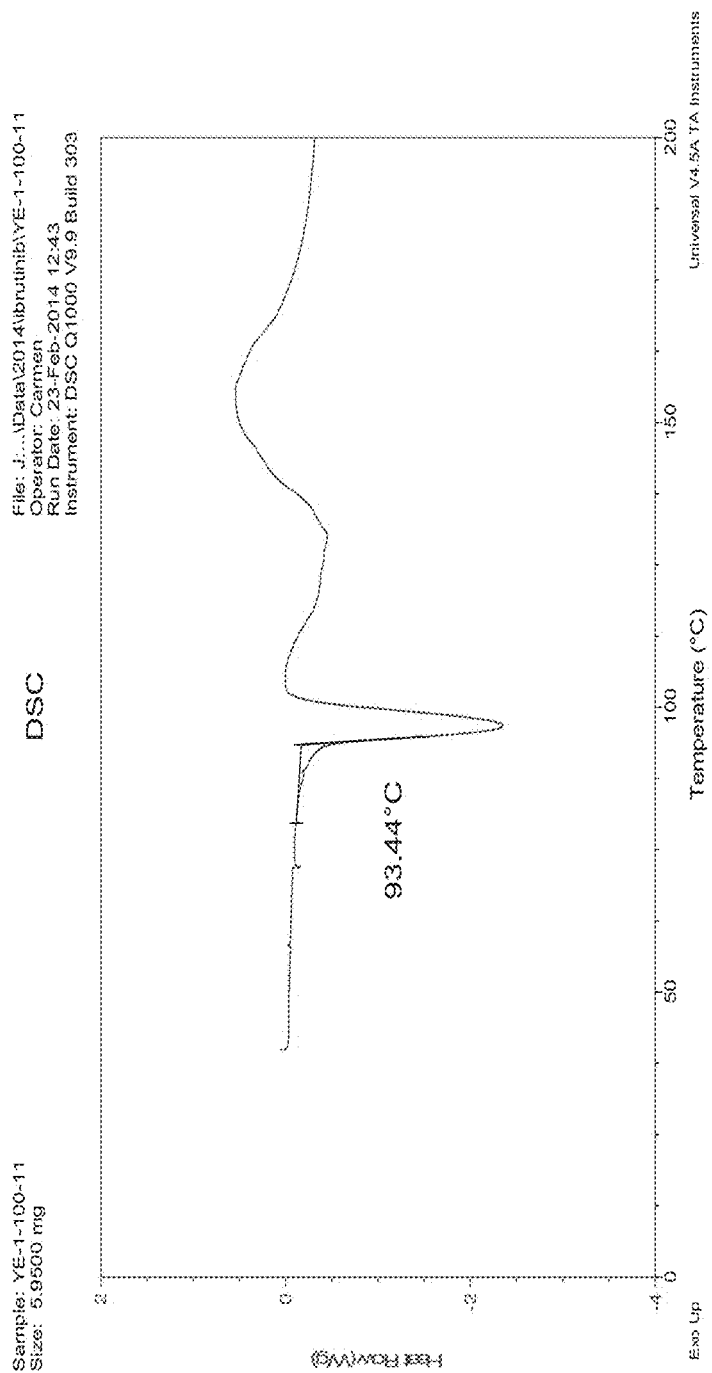
FIG. 9 depicts the DSC curve of crystalline ibrutinib Form VIII.

The DSC curve of crystalline ibrutinib Form VIII is depicted in FIG. 9. It exhibits peak onset at 93.4° C.

Figure 10:
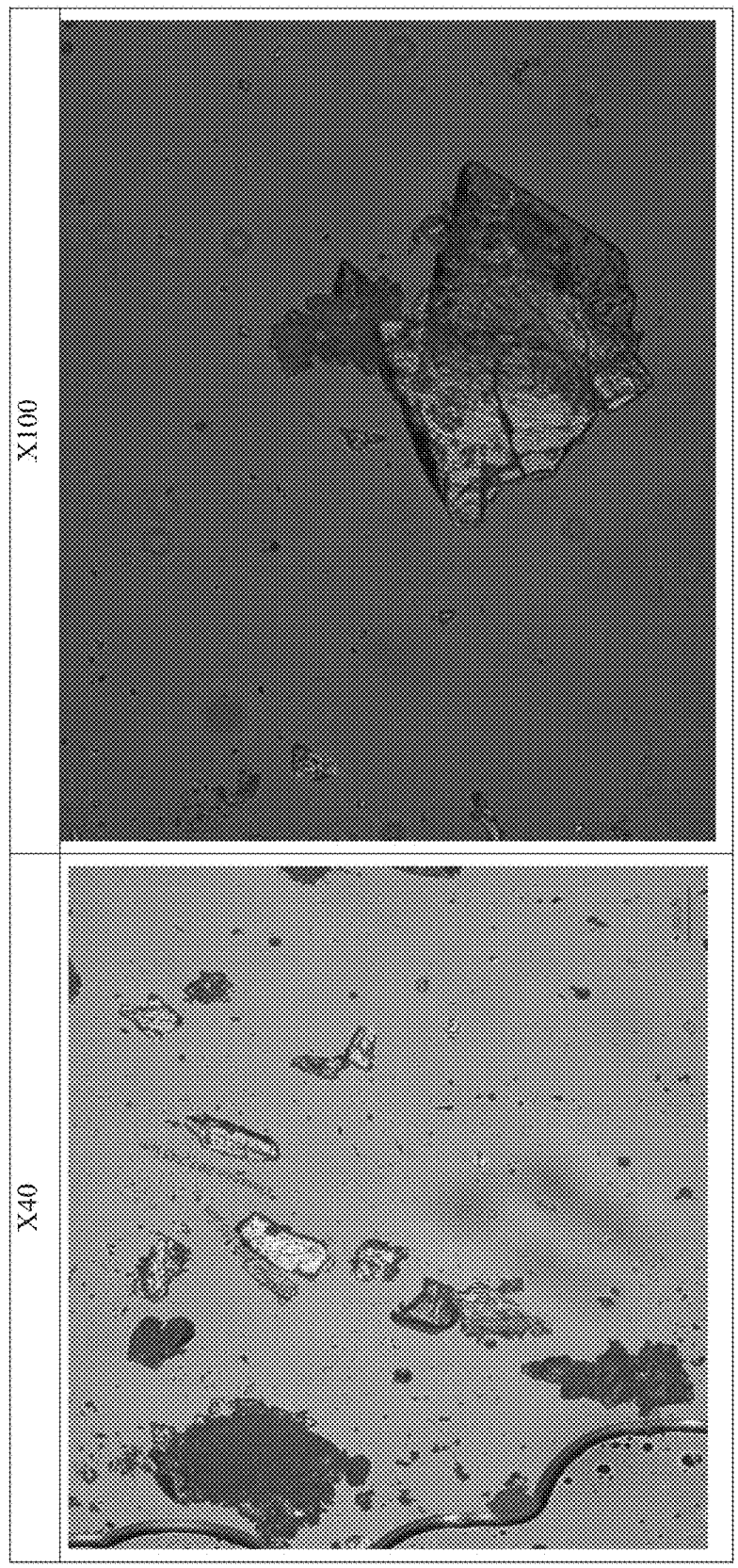
FIG. 10 depicts the optical microscope pictures of crystalline ibrutinib Form VIII.
Figure 11:
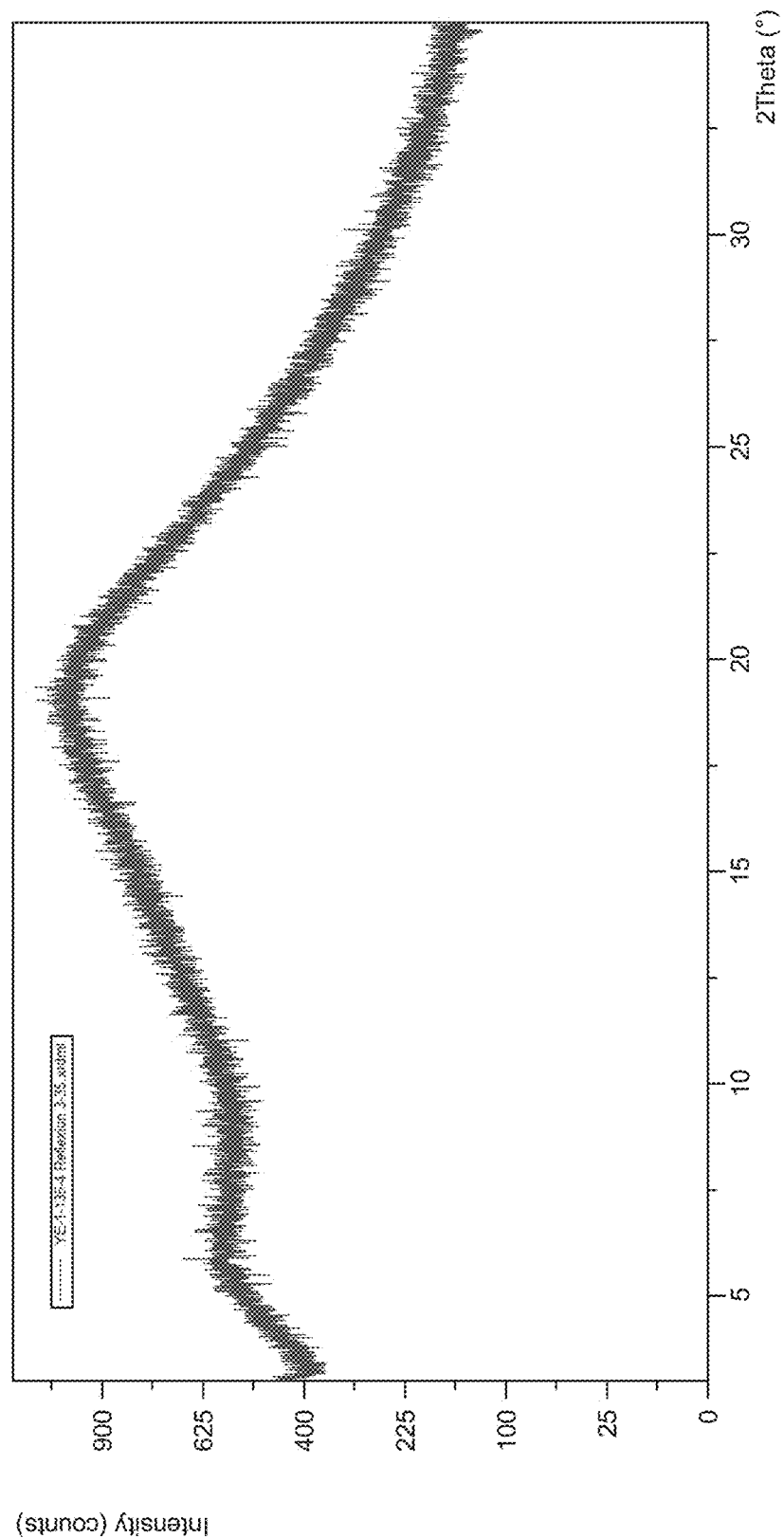
FIG. 11 depicts the XRPD pattern of amorphous ibrutinib prepared by dry ball milling.
Figure 12:
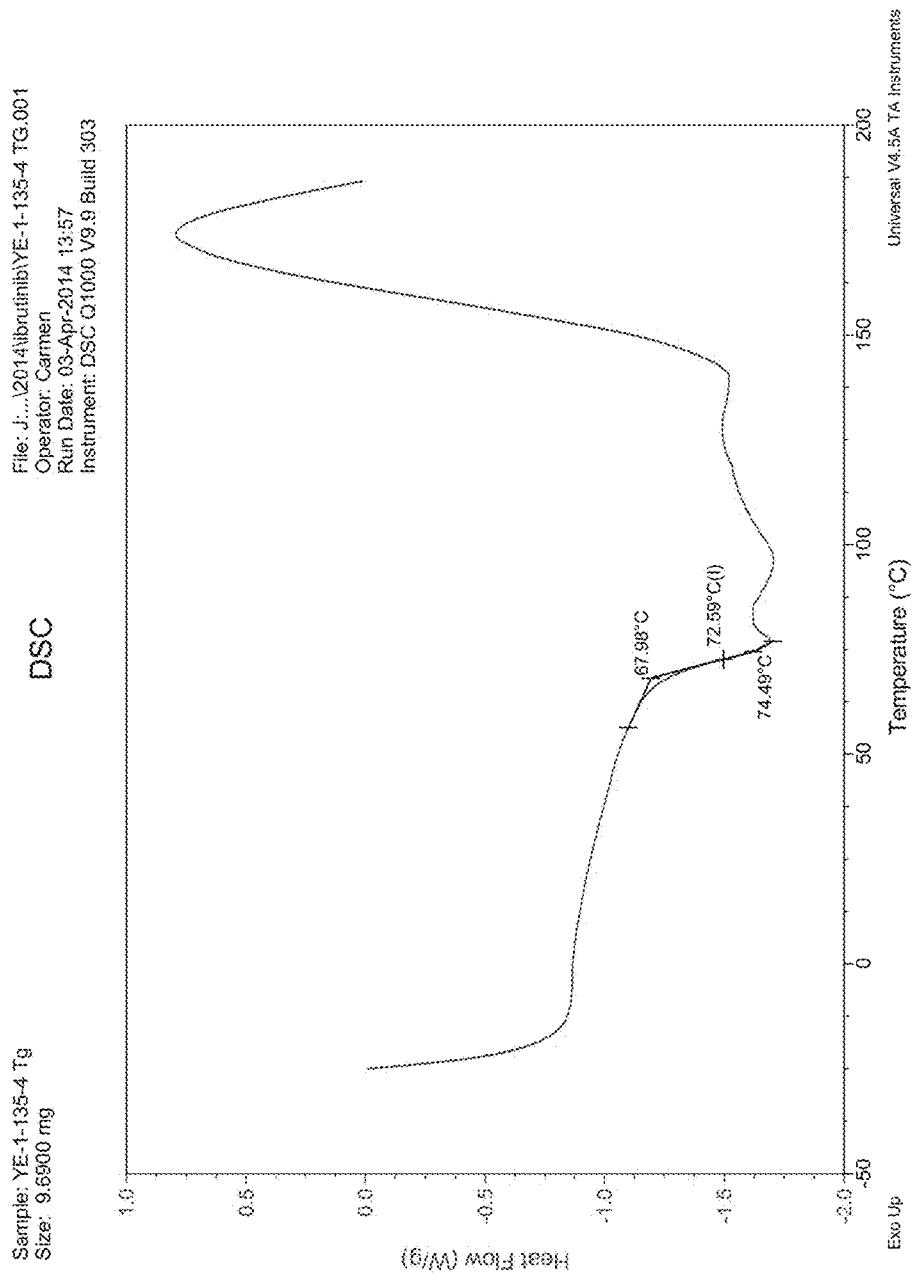
FIG. 12 depicts the DSC curve of amorphous ibrutinib prepared by dry ball milling.
Figure 13:
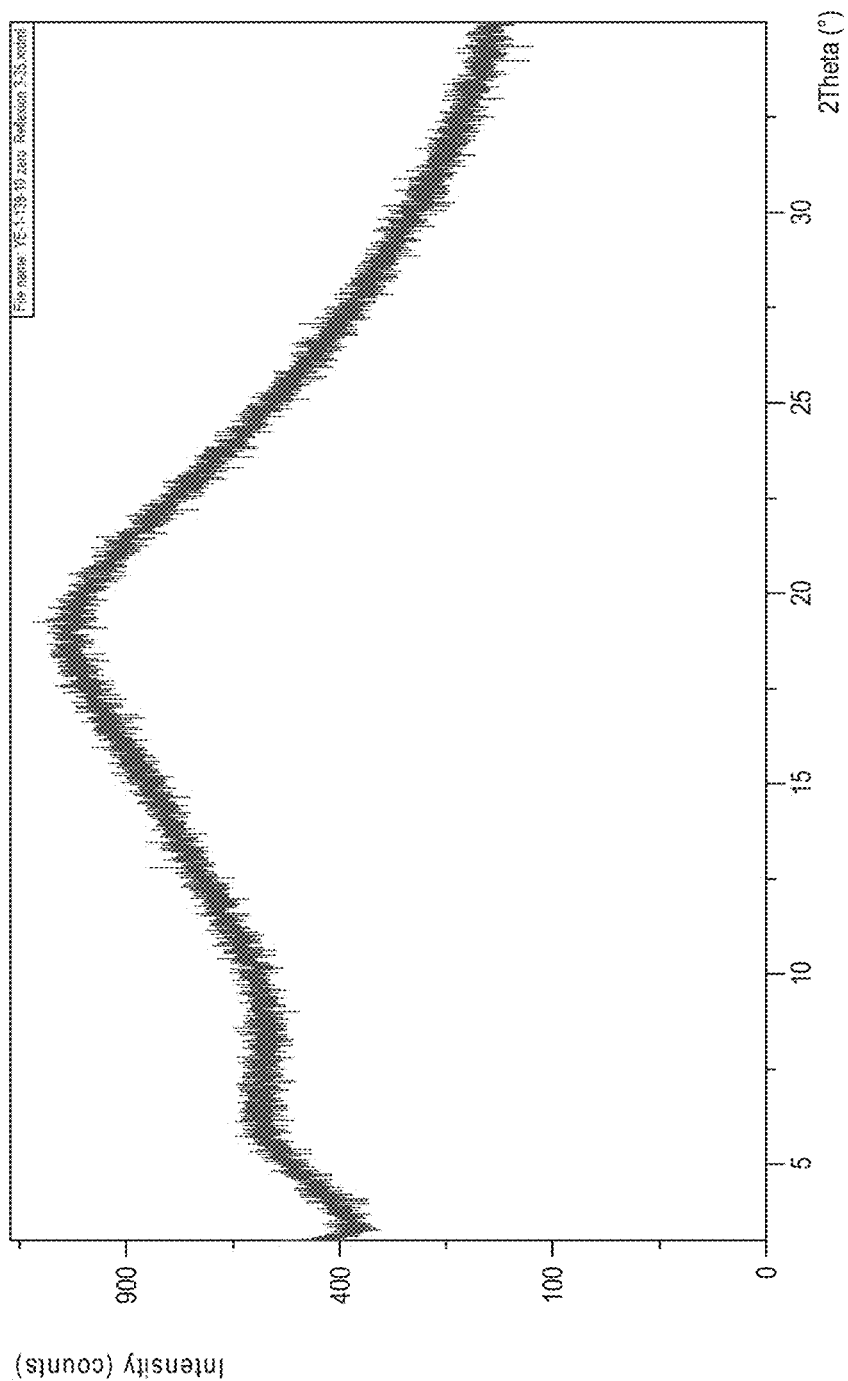
FIG. 13 depicts the XRPD pattern of amorphous ibrutinib prepared by wet ball milling.
Figure 14:
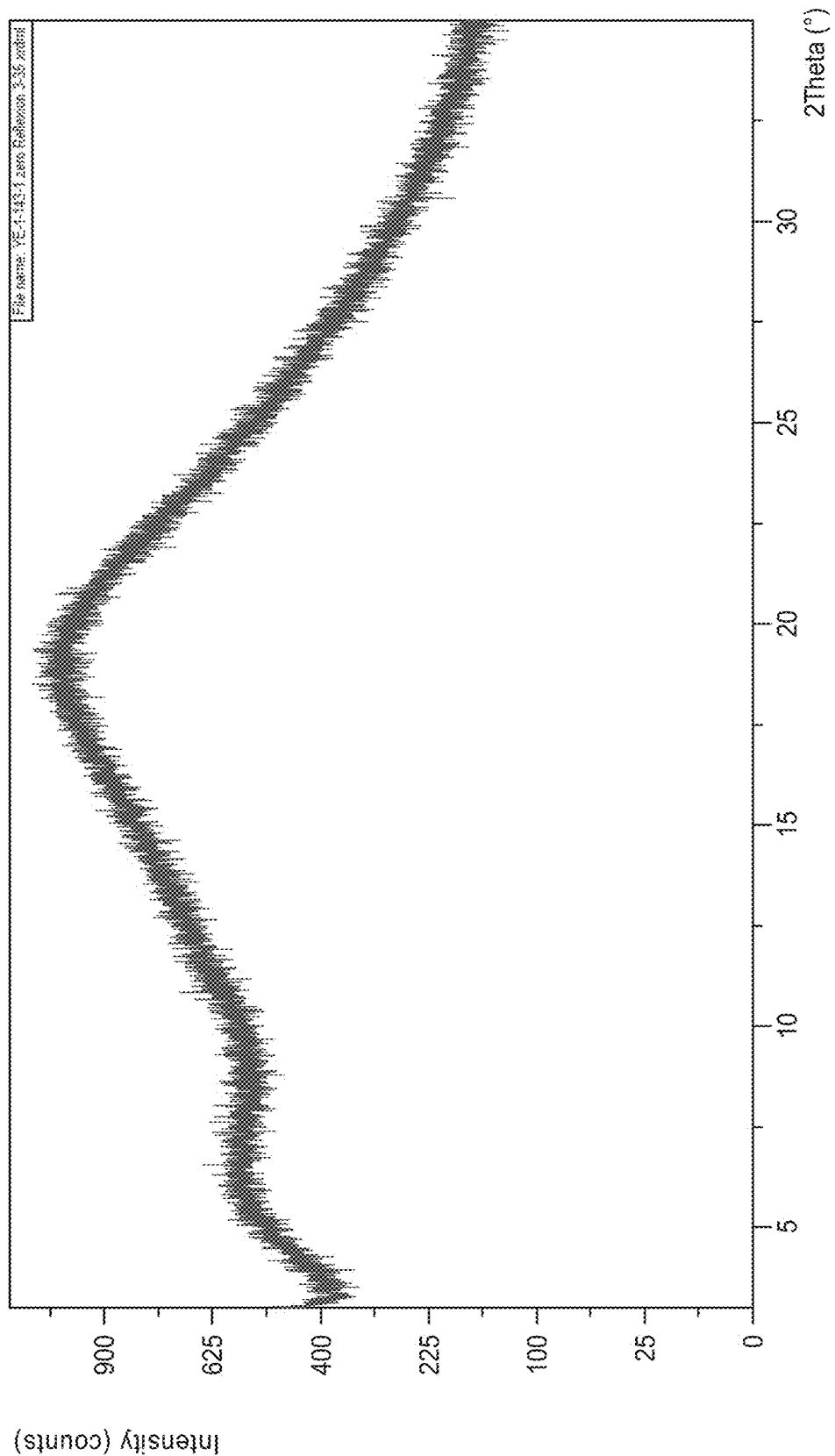
FIG. 14 depicts the XRPD diffraction pattern of amorphous ibrutinib prepared by spray-drying from dichloromethane solution.
Figure 15:
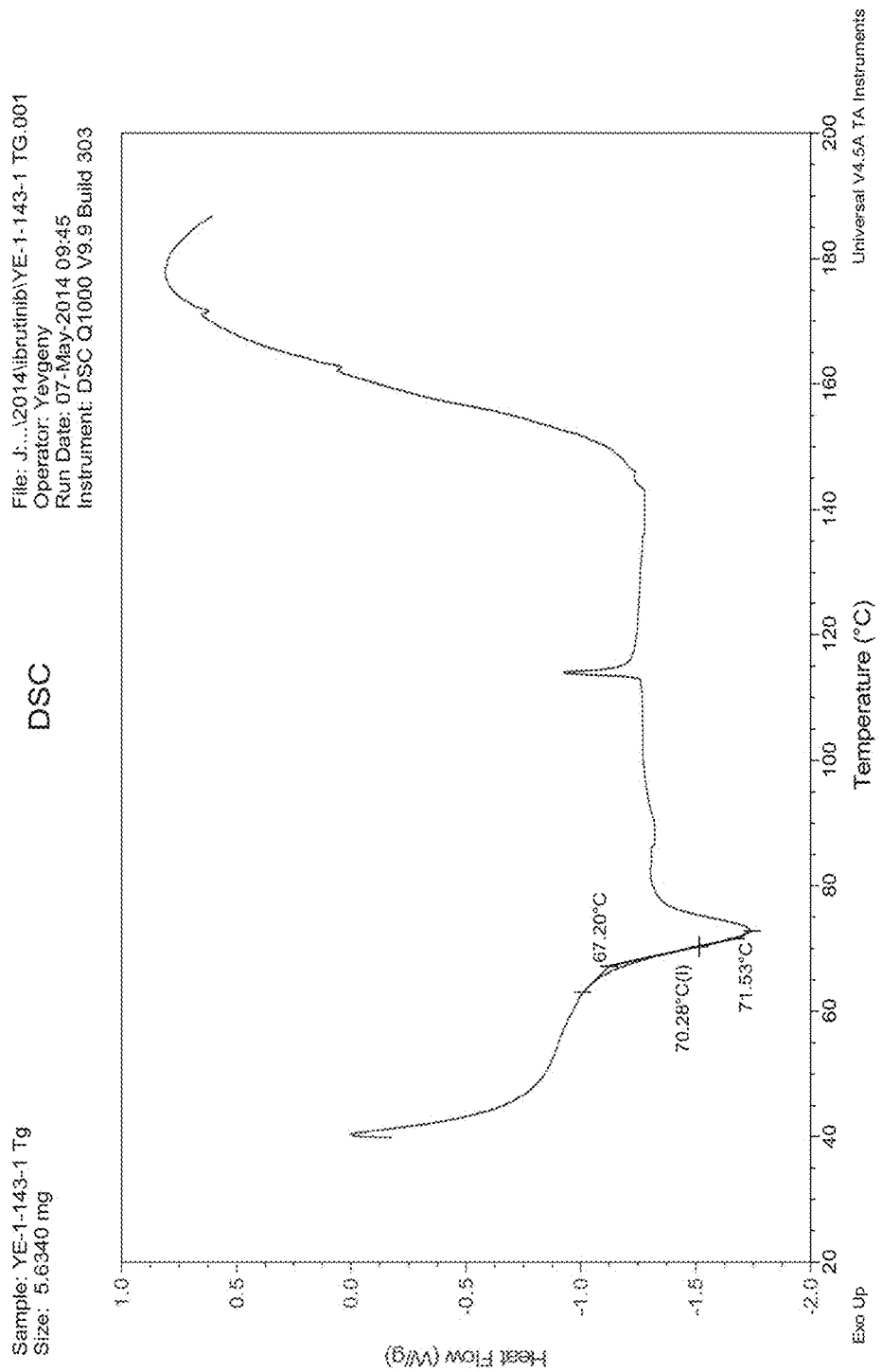
FIG. 15 depicts the DSC curve of amorphous ibrutinib prepared by spray-drying from dichloromethane solution.
Figure 16:
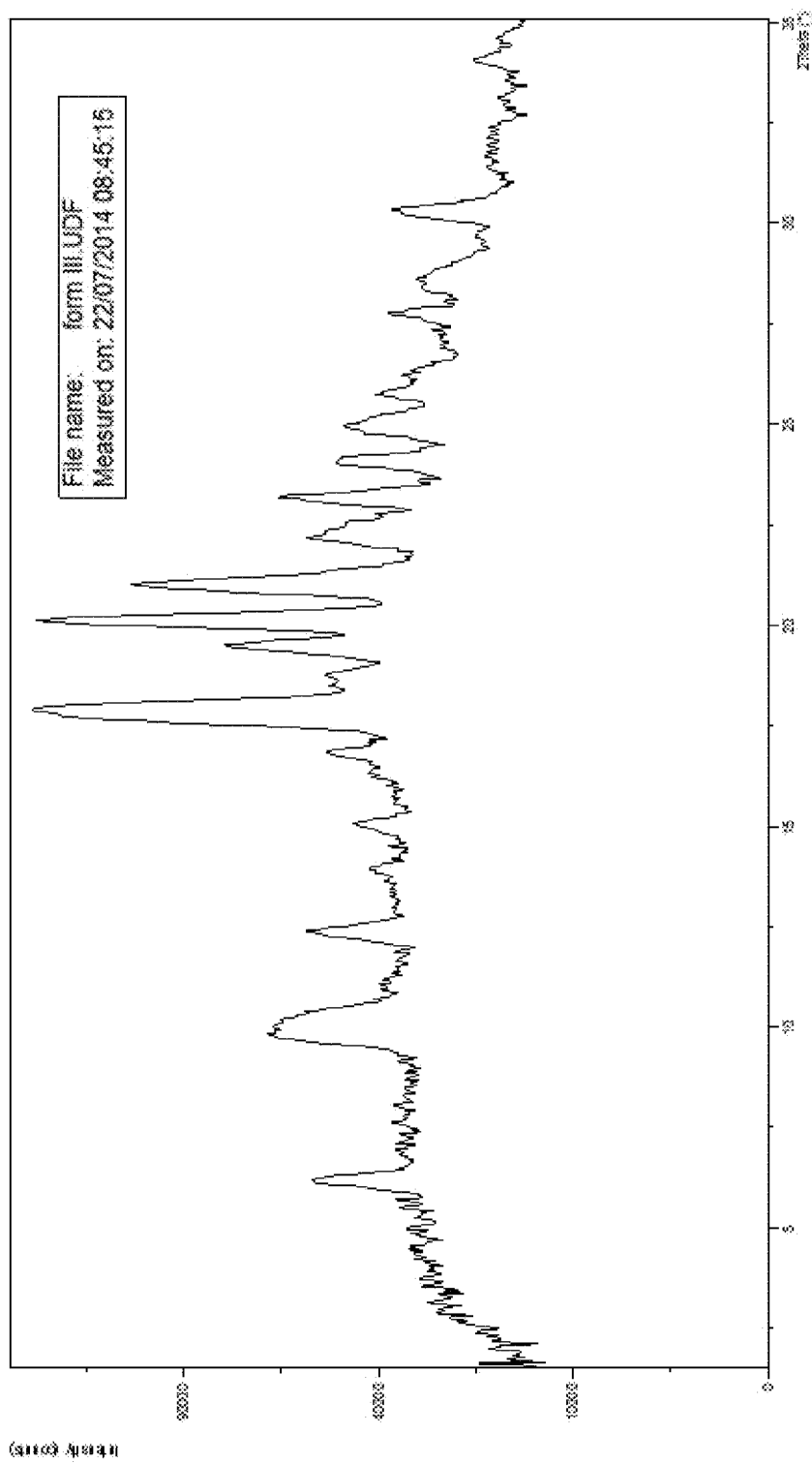
FIG. 16 depicts the XRPD pattern of crystalline ibrutinib Form III.

Optical microscope pictures corresponding to crystalline ibrutinib Form VIII are shown in FIG. 10.

In some embodiments, the present invention provides processes for preparing the ibrutinib polymorphs Form VII or Form VIII. The processes comprise treating ibrutinib with various solvents.

Ibrutinib Form VII or Form VIII can be produced by admixing and optionally heating ibrutinib with a solvent, a mixture of solvents or a mixture of solvent or solvents with anti-solvent or anti-solvents wherein a slurry is obtained, or wherein a solution is obtained. Seeding with the desired polymorph can optionally be employed. The mixture can optionally be cooled before isolation of the solid. When heating is employed, the heating can be done to a controlled temperature. When cooling is employed the cooling is preferably carried out gradually. When seeding is employed the crystals used for seeding correspond to the desired polymorph to be obtained.

According to the present invention, isolation of the solid can be carried out by, e.g., filtration or by removing the solvent, mixture of solvents or mixture of solvent with anti-solvent under reduced pressure.

A process of the present invention for preparing the crystalline ibrutinib Form VII comprises:

dissolving or slurrying ibrutinib in anisole or a mixture of anisole with an additional solvent or an anti-solvent; optionally heating;

optionally adding an anti-solvent;

optionally cooling;

optionally seeding with crystalline ibrutinib Form VII; and isolating the solid and, optionally, drying the solid.

A process of the present invention for preparing the crystalline ibrutinib Form VII comprises: dissolving ibrutinib in a mixture of anisole and acetone with heating; removing the solvents under reduced pressure and, optionally, drying the solid.

A process of the present invention for preparing the crystalline ibrutinib Form VII comprises: dissolving ibrutinib in a mixture of anisole and cyclohexane with heating; removing the solvents under reduced pressure and, optionally, drying the solid.

A process of the present invention for preparing the crystalline ibrutinib Form VII comprises: dissolving ibrutinib in anisole with heating; gradually cooling the solution, isolating the formed solid and, optionally, drying the solid.

A process of the present invention for preparing the crystalline ibrutinib Form VII comprises: dissolving ibrutinib in anisole with heating; adding an anti-solvent, cooling the mixture, isolating the formed solid and, optionally, drying the solid.

A process of the present invention for preparing the crystalline ibrutinib Form VII comprises: dissolving ibrutinib in anisole with heating; adding petroleum ether, cooling the mixture, isolating the formed solid and, optionally, drying the solid.

A process of the present invention for preparing the crystalline ibrutinib Form VII comprises: dissolving ibrutinib in anisole with heating; adding isooctane, cooling the mixture, isolating the formed solid and, optionally, drying the solid.

A process of the present invention for preparing the crystalline ibrutinib Form VII comprises: dissolving ibrutinib in anisole with heating; adding xylene, cooling the mixture, isolating the formed solid and, optionally, drying the solid.

A process of the present invention for preparing the crystalline ibrutinib Form VII comprises: slurrying ibrutinib in anisole with heating; cooling the mixture, isolating the formed solid and, optionally, drying the solid.

A process of the present invention for preparing the crystalline ibrutinib Form VIII comprises: dissolving ibrutinib in chlorobenzene or a mixture of chlorobenzene with another solvent with heating, cooling the solution, isolating the formed solid and, optionally, drying the solid.

A process of the present invention for preparing the crystalline ibrutinib Form VIII comprises: dissolving ibrutinib in chlorobenzene with heating, cooling the solution, isolating the formed solid and, optionally, drying the solid.

A process of the present invention for preparing the crystalline ibrutinib Form VIII comprises: dissolving ibrutinib in a mixture of chlorobenzene and toluene with heating; removing the solvents under reduced pressure and, optionally, drying the solid. According to a specific embodiment of the present invention a process for preparing ibrutinib crystalline Form VII in accordance with the present invention includes the steps of dissolving ibrutinib in anisole while heating to a temperature of about 77° C. under controlled stirring, cooling gradually to a temperature of about 5° C., removing the liquid by filtration and drying to afford crystals of ibrutinib Form VII having characterized XRPD pattern as depicted in FIG. 1 and Table 1.

According to a specific embodiment of the present invention a process for preparing ibrutinib crystalline Form VII in accordance with the present invention includes the steps of admixing ibrutinib with anisole at a temperature of about 50° C. under controlled stirring, adding petroleum ether drop-wise to the mixture to afford formation of a solid, removing the liquid by filtration and drying. Crystals of ibrutinib Form VII are obtained having characterized XRPD pattern as depicted in FIG. 1 and Table 1.

According to a specific embodiment of the present invention a process for preparing ibrutinib crystalline Form VII in accordance with the present invention includes the steps of mixing ibrutinib with anisole at a temperature of about 60° C., slowly cooling to 5° C. overnight and seeding with crystals of crystalline ibrutinib Form VII, removing the liquid by filtration and drying to afford crystals of ibrutinib Form VII having characterized XRPD pattern as depicted in FIG. 1 and Table 1.

According to a specific embodiment of the present invention a process for preparing ibrutinib crystalline Form VIII in accordance with the present invention includes the steps of dissolving ibrutinib in chlorobenzene with heating to a temperature of about 80° C. under controlled stirring, cooling gradually to a temperature of about 5° C., removing the liquid by filtration and drying to afford crystals of ibrutinib Form VIII having characterized XRPD pattern as depicted in FIG. 6 and Table 2.

According to a specific embodiment of the present invention a process for preparing ibrutinib crystalline Form VIII in accordance with the present invention includes the steps of dissolving ibrutinib in chlorobenzene with heating to about 65° C., cooling gradually to a temperature of about 4° C. overnight, removing the liquid by filtration and drying to afford crystals of ibrutinib Form VIII having characterized XRPD pattern as depicted in FIG. 6 and Table 2.

According to a specific embodiment of the present invention a process for preparing ibrutinib crystalline Form VIII in accordance with the present invention includes the steps of dissolving ibrutinib in a mixture of chlorobenzene and toluene at a temperature of 50° C. and evaporating the solvent mixture under vacuum to afford a solid. The solid is dried to afford crystals of ibrutinib Form VIII having characterized XRPD pattern as depicted in FIG. 6 and Table 2.

Preferably, the solvent used to obtain the ibrutinib polymorph VII in accordance with the present invention is anisole. Yields of at least 80% or at least 90% can be obtained.

Preferably, the solvent used to obtain the ibrutinib polymorph VIII in accordance with the present invention is chlorobenzene. Yields of at least 80% or at least 90% can be obtained.

The process of the present invention can produce crystalline ibrutinib Form VII or Form VIII in a purity of at least about 98%, and preferably in a purity of at least about 99.5%.

Any suitable ratio of ibrutinib to solvent, a mixture of solvents or a mixture of solvent or solvents with anti-solvent or anti-solvents can be used. A preferred ratio between ibrutinib and solvent, mixture of solvents or a mixture of solvent or solvents with anti-solvent or anti-solvents is between about 1 g ibrutinib: 50 ml to about 1g ibrutinib: 1 ml.

In some embodiments heating is carried out after ibrutinib is mixed with the solvent, mixture of solvents or a mixture of solvent or solvents with anti-solvent or anti-solvents. Preferably heating is carried out to a controlled temperature. The heating is preferably carried out with stirring. In some embodiments the heating is at least to 40° C. Preferably, heating is carried out to a temperature from about 40° C. to about 90° C.

In some embodiments, cooling is carried out gradually. Preferred temperatures for cooling are below 40° C. Most preferably, cooling is carried out gradually to a temperature of about 5° C.

The present invention provides pharmaceutical compositions comprising at least one of the crystalline forms of ibrutinib of the present invention, e.g., Form VII or Form VIII and pharmaceutically acceptable excipients.

The present invention also provides a process for preparing the pharmaceutical compositions comprising at least one of the crystalline forms of ibrutinib of the present invention and pharmaceutically acceptable excipients.

Pharmaceutical compositions can be prepared by mixing the crystalline forms of ibrutinib of the present invention, e.g., Form VII or Form VIII, optionally with additional active ingredients, with inactive ingredients such as absorption accelerators, binders, bulking agents, carriers, diluents, disintegrants, fillers, lubricants, surface-active agents, wetting agents and the like.

The pharmaceutical compositions of the present invention can be administered, for example, as tablets, pills, powders, liquids, suspensions, emulsions, granules, capsules, suppositories, injection preparations (solutions and suspensions), and the like.

The present invention further provides methods of using the ibrutinib crystalline forms of the present invention, e.g., Form VII or Form VIII in the treatment of diseases or conditions including diseases or conditions for which ibrutinib provides therapeutic benefit to a mammal having the disease or condition, such as, Mantle Cell Lymphoma (MCL) and Chronic Lymphocytic Leukemia (CLL) by administering to a subject in need thereof a therapeutically effective amount of ibrutinib Form VII or ibrutinib Form VIII.

The inventors of the present invention have surprisingly discovered additional novel crystalline forms of ibrutinib that are named herein crystalline ibrutinib Form III, crystalline ibrutinib Form IV, crystalline ibrutinib Form V, crystalline ibrutinib Form VI and crystalline ibrutinib Form IX.

The present invention additionally provides processes for preparing the crystalline ibrutinib Form III, Form IV, Form V, Form VI, Form VII and Form IX. The starting material in these processes can be produced by any suitable method, including synthesis methods known in the art. For example, the ibrutinib starting material is obtained as described in Routes 1-3 of Example 1 of International Patent Publication No. WO2013/184572, entitled "Crystalline forms of a Bruton's tyrosine kinase inhibitor".

The processes of the present invention can produce high purity crystalline ibrutinib Form III, Form IV, Form V, Form VI, Form VII and Form IX. In addition, the processes of the present invention can produce stable and slightly hygroscopic amorphous ibrutinib.

The present invention additionally provides stable amorphous forms of ibrutinib. In specific embodiments of the present invention the stable amorphous ibrutinib is slightly hygroscopic. In addition, the present invention provides processes for producing said amorphous ibrutinib forms. In one embodiment of the present invention a process is provided for producing a stable, slightly hygroscopic amorphous ibrutinib form.

As used herein, the term AAC refers to Accelerated Aging Conditions, which comprises using aggravated conditions of heat and humidity to speed up the normal aging process of a chemical compound in order to determine the long term effects of expected levels of stress within a short time period.

As used herein, the term VDS refers to Vapor Diffusion into Solids technique, which comprises exposing a solid chemical compound, placed in, e.g., an open glass vessel to the vapors of a solvent, usually at ambient temperature for a certain period of time.

As used herein, the term VDL refers to Vapor Diffusion into Liquids technique, which comprises exposing a solution, which can be a saturated solution, of a chemical compound, placed in, e.g., an open glass vessel or a vial to the vapors of a solvent, usually at ambient temperature for a certain period of time.

As used herein, the term TCP refers to thermal cycling, which is the process of cycling through two temperatures at relatively high rate of change.

The X-ray powder diffraction pattern corresponding to crystalline ibrutinib Form III is depicted in FIG. 6 and Table 3. The strong diffraction peaks at 17.90, 19.50, 20.10 and 21.02±0.2 degrees 2θ are most characteristic of this form. The X-ray powder diffraction peak positions and intensities exhibited by crystalline ibrutinib Form III are listed in Table 3.

TABLE 3

| No. | Position [°2θ] | Relative Intensity [%] | d-spacing [Å] |
| --- | --- | --- | --- |
| 1 | 6.18 | 20.8 | 14.28 |
| 2 | 12.38 | 19.7 | 7.14 |
| 3 | 16.82 | 13.1 | 5.26 |
| 4 | 17.90 | 100 | 4.95 |
| 5 | 19.50 | 36.9 | 4.55 |
| 6 | 20.10 | 94.6 | 4.41 |
| 7 | 21.02 | 64.4 | 4.22 |
| 8 | 23.14 | 27.2 | 3.84 |
| 9 | 24.10 | 19.9 | 3.69 |
| 10 | 25.78 | 13.1 | 3.45 |
| 11 | 27.74 | 14.1 | 3.21 |
| 12 | 30.30 | 17.1 | 2.95 |

Figure 17:
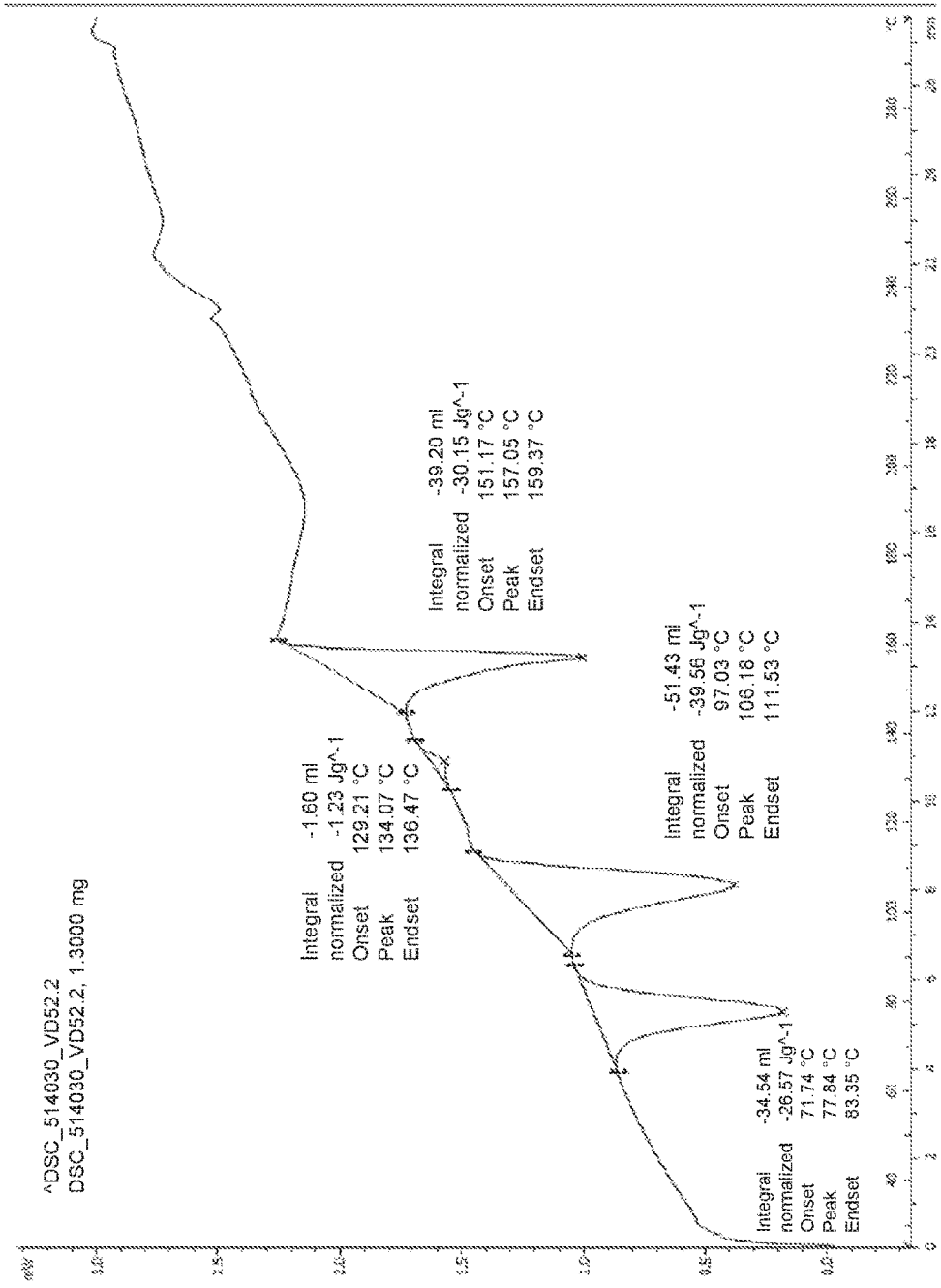
FIG. 17 depicts the DSC curve of crystalline ibrutinib Form III.

The DSC curve of crystalline ibrutinib Form III is depicted in FIG. 17.

In one embodiment of the present invention ibrutinib crystalline Form III is a 1,4-dioxane solvate.

Figure 18:
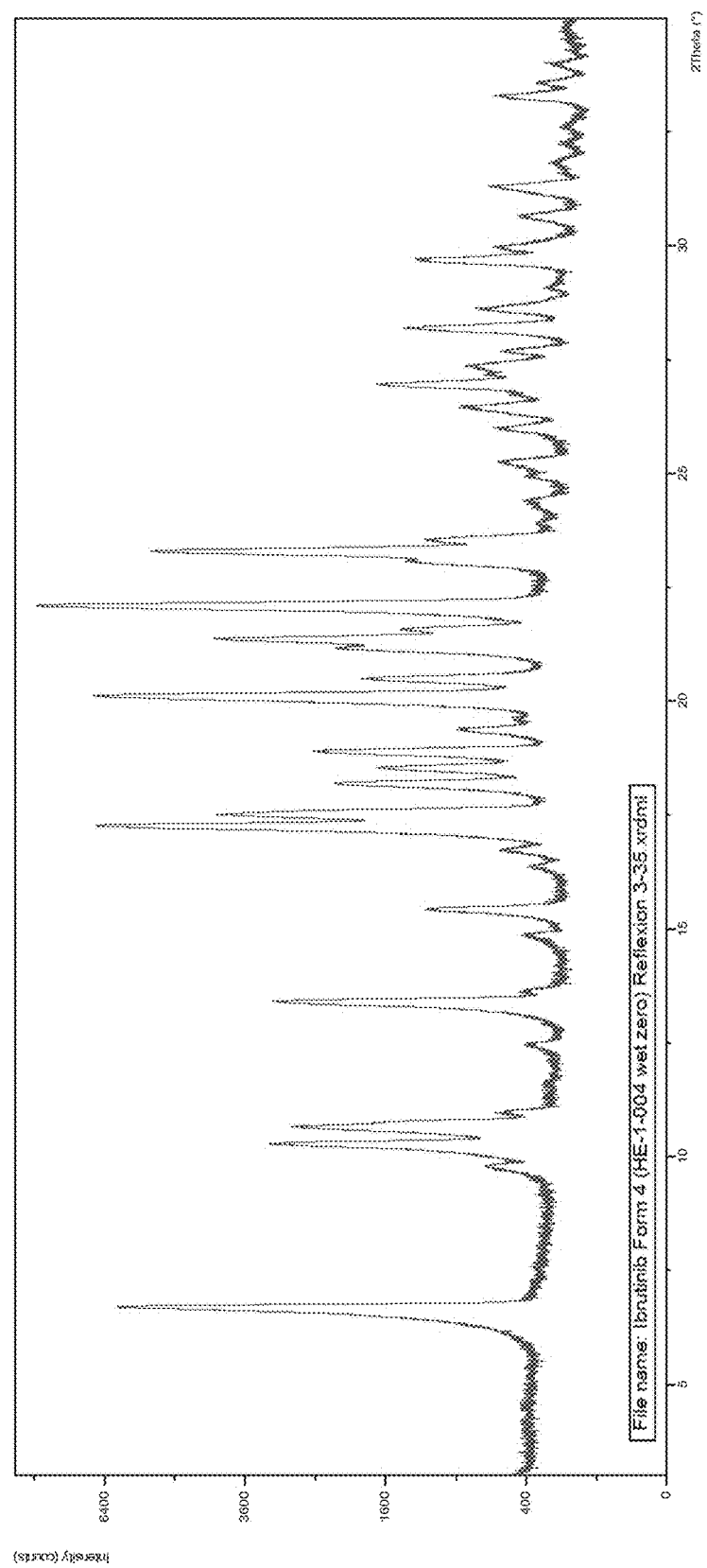
FIG. 18 depicts the XRPD pattern of crystalline ibrutinib Form IV.

The X-ray powder diffraction pattern corresponding to crystalline ibrutinib Form IV is depicted in FIG. 18 and Table 4. The strong diffraction peaks at 17.34, 20.10, 21.30 and 22.06±0.2 degrees 2θ are most characteristic of this form. The X-ray powder diffraction peak positions and intensities exhibited by crystalline ibrutinib Form IV are listed in Table 4.

TABLE 4

| No. | Position [°2θ] | Relative Intensity [%] | d-spacing [Å] |
|---|---|---|---|
| 1 | 6.70 | 37.5 | 13.18 |
| 2 | 9.74 | 12.7 | 9.07 |
| 3 | 10.66 | 44.0 | 8.29 |
| 4 | 13.38 | 16.3 | 6.61 |
| 5 | 15.42 | 11.8 | 5.74 |
| 6 | 17.34 | 61.2 | 5.11 |
| 7 | 18.18 | 19.9 | 4.87 |
| 8 | 19.38 | 16.3 | 4.57 |
| 9 | 20.10 | 72.8 | 4.41 |
| 10 | 21.30 | 100 | 4.17 |
| 11 | 22.06 | 55.0 | 4.02 |
| 12 | 23.30 | 29.7 | 3.81 |
| 13 | 25.22 | 21.5 | 3.53 |
| 14 | 27.70 | 18.7 | 3.22 |

Figure 19:
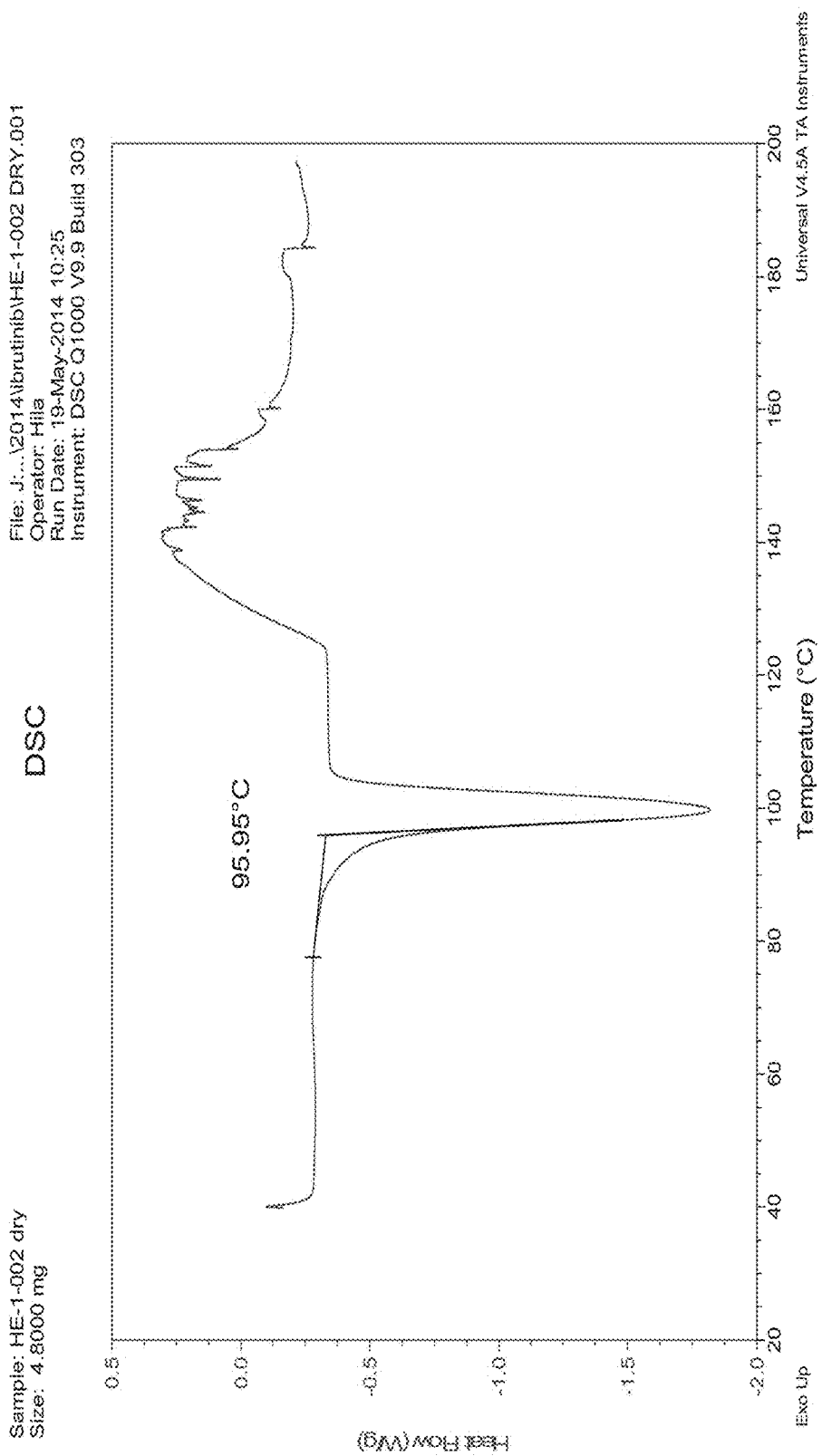
FIG. 19 depicts the DSC curve of crystalline ibrutinib Form IV.

The DSC curve of crystalline ibrutinib Form IV is depicted in FIG. 19. It exhibits peak onset at 95.95° C.

Figure 20:
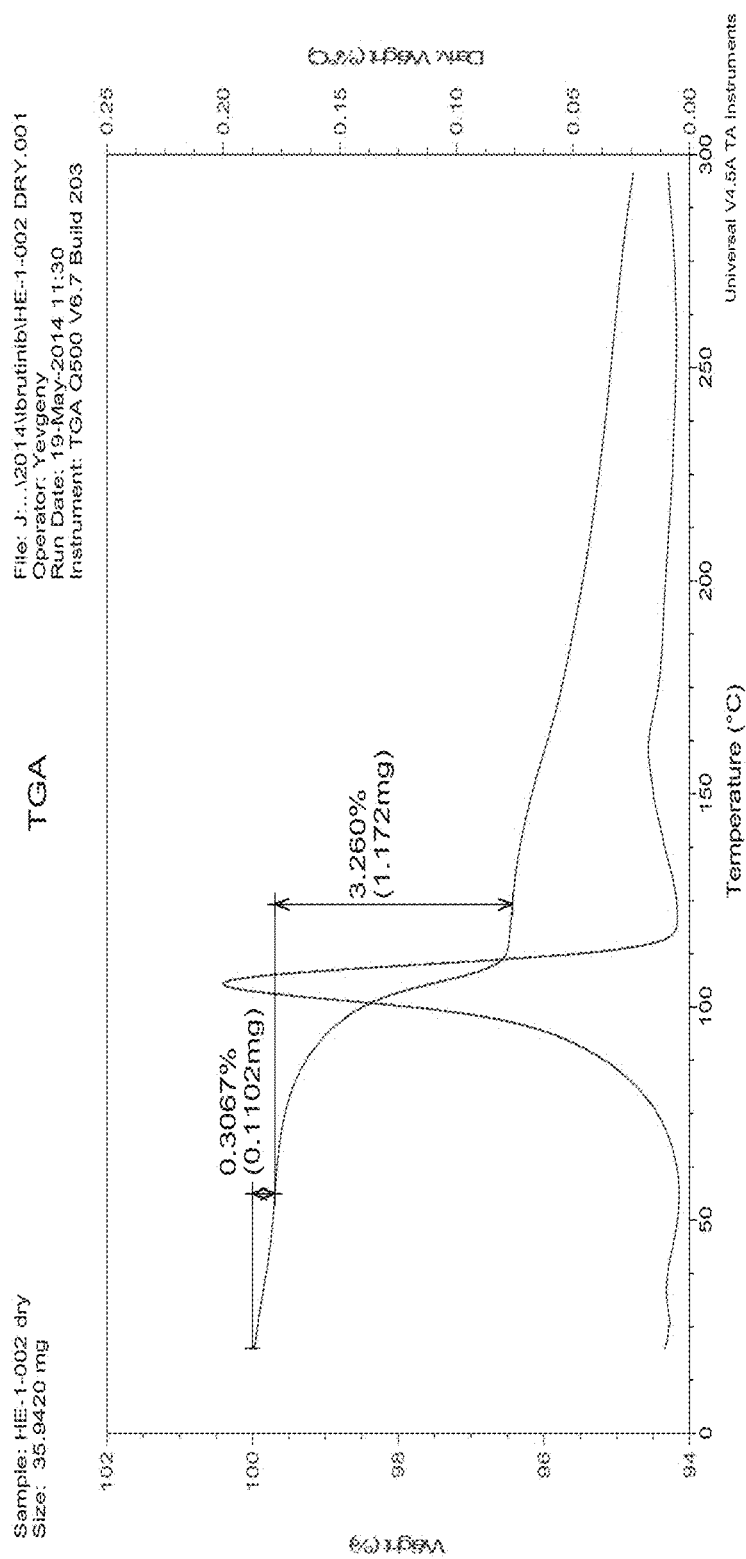
FIG. 20 depicts the Thermo Gravimetric Analysis (TGA) curve of crystalline ibrutinib Form IV.
Figure 21:
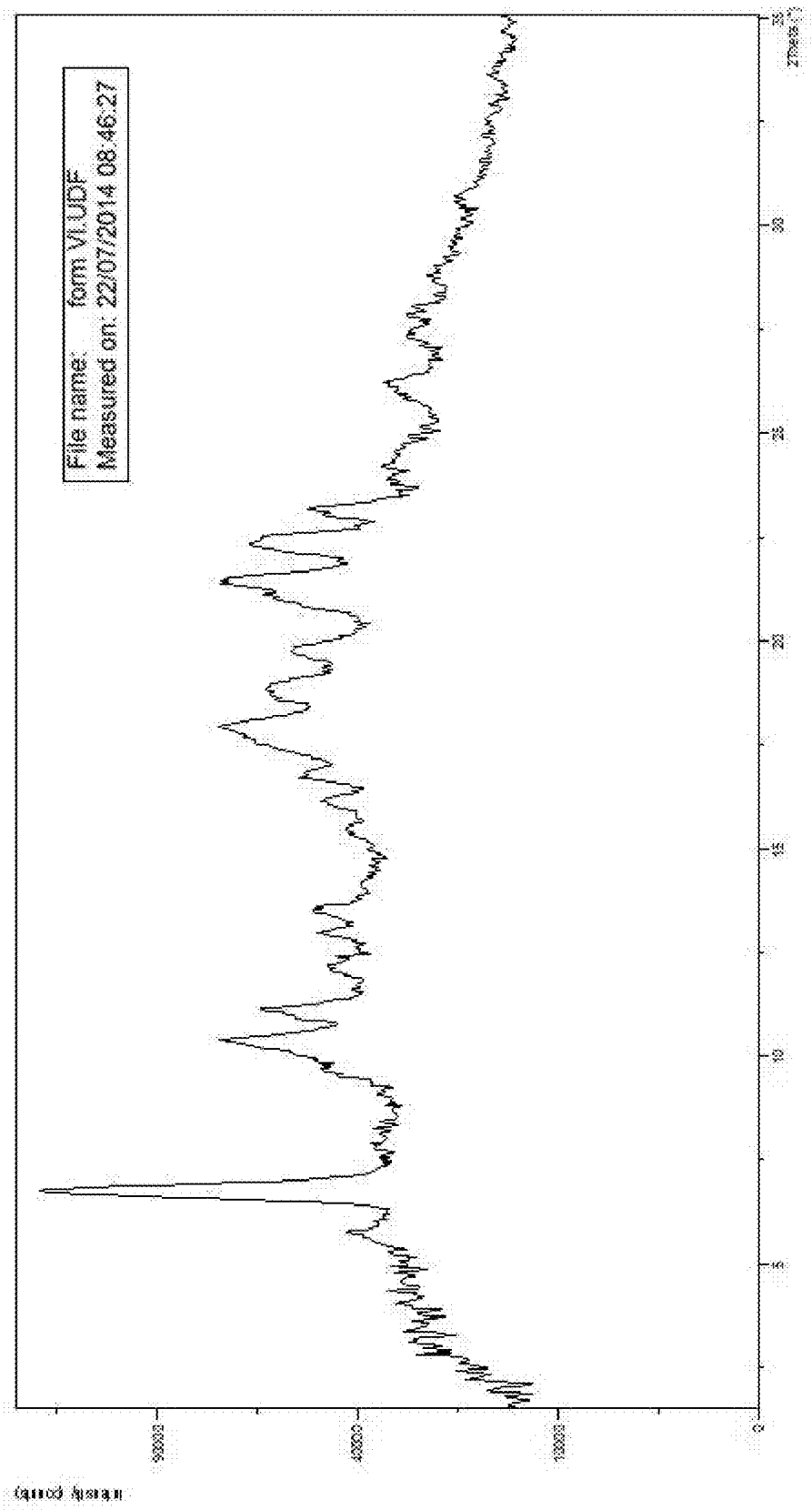
FIG. 21 depicts the X-ray powder diffraction pattern corresponding to crystalline ibrutinib Form VI.

The TGA curve of crystalline ibrutinib Form IV is depicted in FIG. 20.

In one embodiment of the present invention, ibrutinib crystalline Form IV is a 1,2-dimethoxyethane solvate.

The X-ray powder diffraction peak positions and intensities exhibited by crystalline ibrutinib Form V are listed in Table 5. The strong diffraction peaks at 6.26, 9.98, 18.06, 19.78 and 22.94±0.2 degrees 2θ are most characteristic of this form.

TABLE 5

| No. | Position [°2θ] | Relative Intensity [%] | d-spacing [Å] |
|---|---|---|---|
| 1 | 3.22 | 16.7 | 27.41 |
| 2 | 3.98 | 12.0 | 22.17 |
| 3 | 6.26 | 85.5 | 14.10 |
| 4 | 8.18 | 4.9 | 10.80 |
| 5 | 9.98 | 60.0 | 8.85 |
| 6 | 12.58 | 23.6 | 7.03 |
| 7 | 18.06 | 100 | 4.91 |
| 8 | 19.78 | 76.2 | 4.48 |
| 9 | 20.54 | 30.6 | 4.32 |
| 10 | 21.22 | 34.0 | 4.18 |
| 11 | 22.94 | 46.8 | 3.87 |
| 12 | 25.62 | 14.0 | 3.47 |
| 13 | 27.50 | 28.0 | 3.24 |

In one embodiment of the present invention crystalline ibrutinib Form V is a methanol solvate of ibrutinib.

Figure 22:
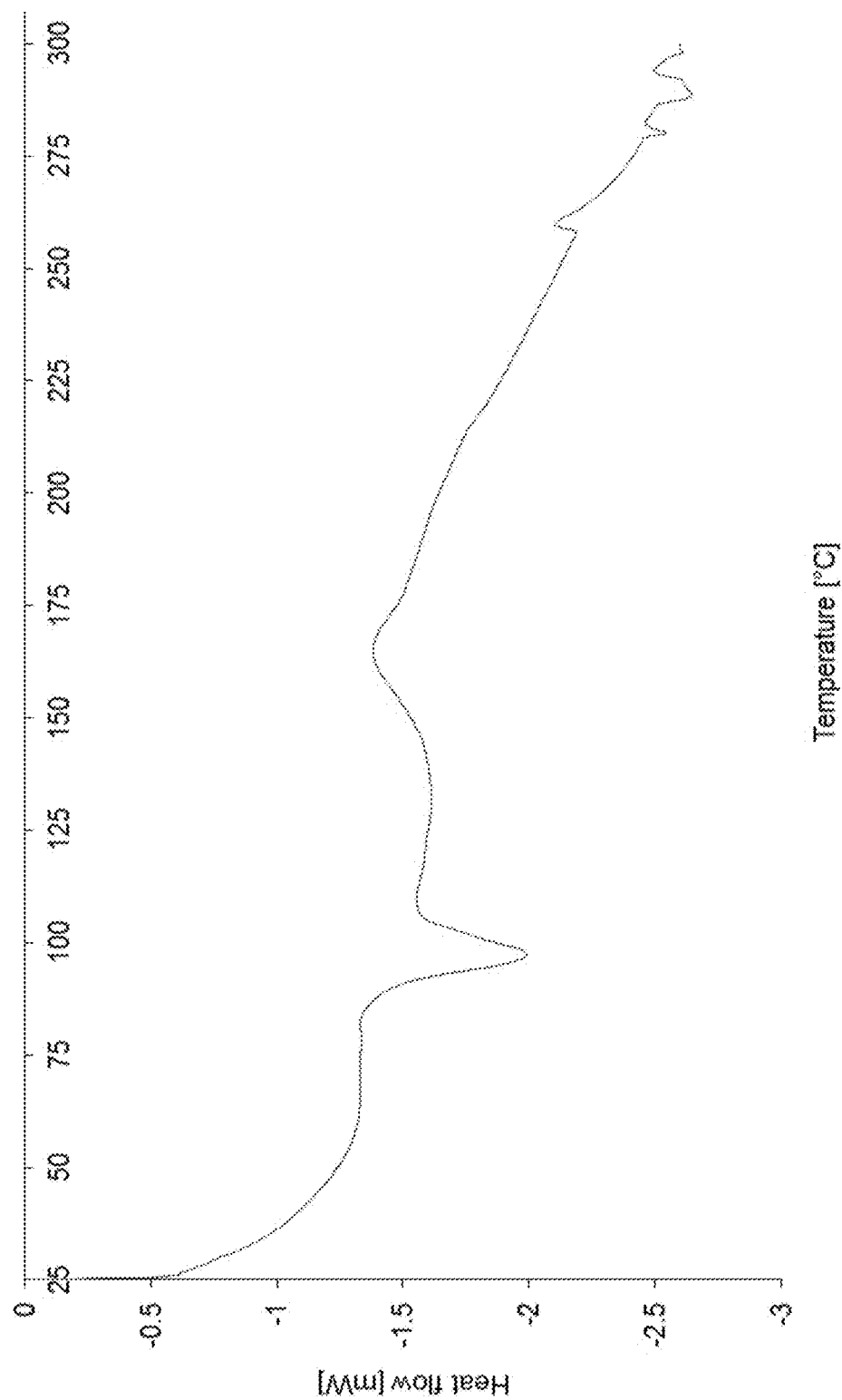
FIG. 22 depicts the DSC curve of crystalline ibrutinib Form VI.

The X-ray powder diffraction pattern corresponding to crystalline ibrutinib Form VI is depicted in FIG. 22.

The X-ray powder diffraction peak positions and intensities exhibited by crystalline ibrutinib Form VI are listed in Table 6. The strong diffraction peaks at 6.74, 10.34, 17.94 and 21.46±0.2 degrees 2θ are most characteristic of this form.

TABLE 6

| No. | Position [°2θ] | Relative Intensity [%] | d-spacing [Å] |
|---|---|---|---|
| 1 | 6.74 | 100 | 13.1 |
| 2 | 10.34 | 40.0 | 8.55 |
| 3 | 11.10 | 28.1 | 7.96 |

TABLE 6-continued

| No. | Position [°2θ] | Relative Intensity [%] | d-spacing [Å] |
|---|---|---|---|
| 4 | 12.98 | 13.1 | 6.81 |
| 5 | 16.78 | 14.3 | 5.28 |
| 6 | 17.94 | 35.9 | 4.94 |
| 7 | 19.74 | 17.8 | 4.49 |
| 8 | 21.46 | 40.1 | 4.14 |
| 9 | 22.38 | 33.2 | 3.97 |
| 10 | 23.14 | 19.0 | 3.84 |

The DSC curve of crystalline ibrutinib Form VI is depicted in FIG. 22.

In one embodiment of the present invention, ibrutinib Form VI is an anhydrous, stable crystalline ibrutinib form. After placing a vial containing Form VI in a climate chamber at 40° C. and 75% for 3 days, the solid was collected and checked by XRPD. The analysis confirmed that Form VI was fully retained.

Figure 23:
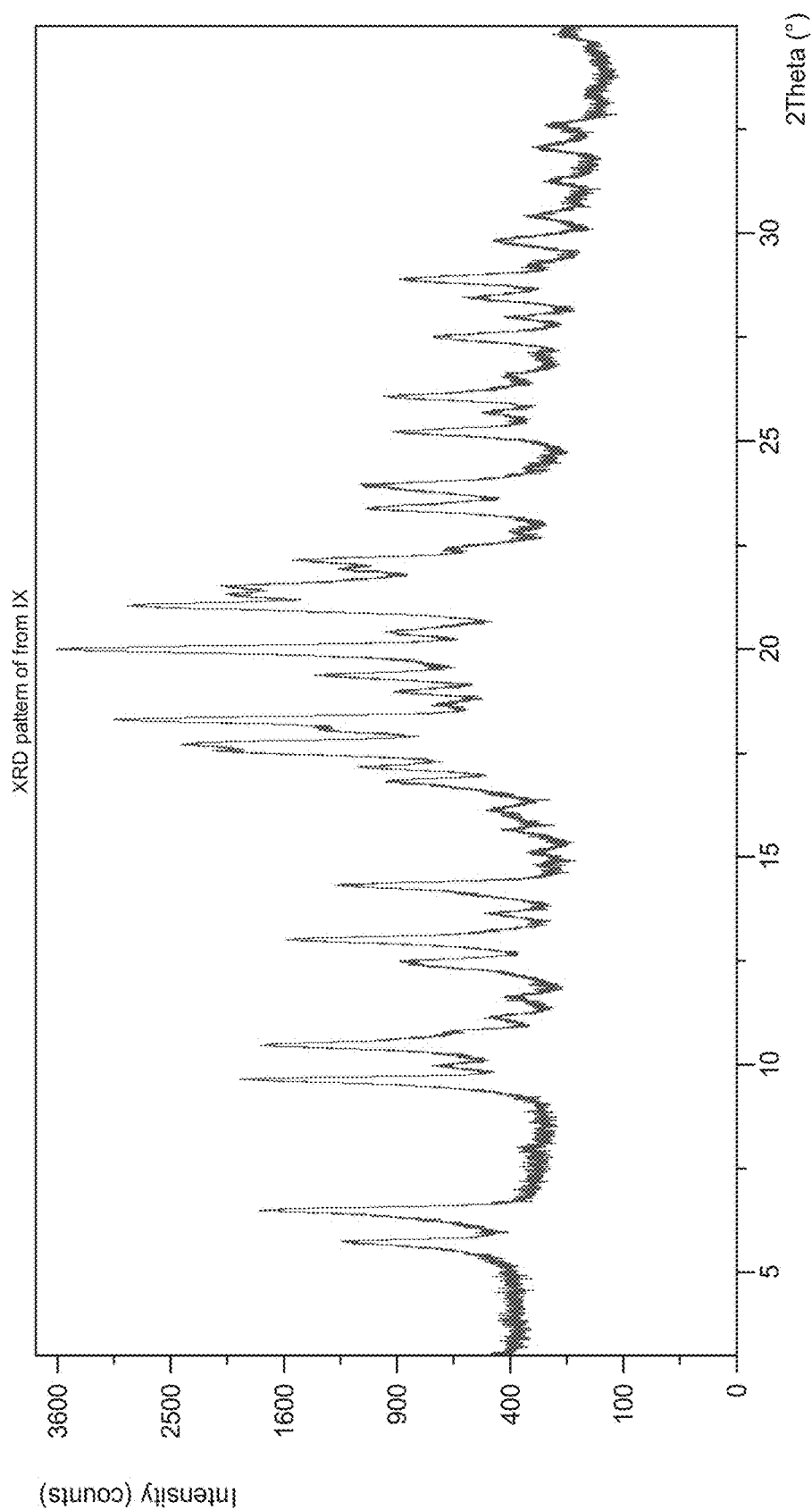
FIG. 23 depicts the XRPD pattern of crystalline ibrutinib Form IX

The X-ray powder diffraction pattern corresponding to crystalline ibrutinib Form IX is depicted in FIG. 23 and Table 7. The strong diffraction peaks at 9.6, 10.5, 17.7, 18.3, 20.0, 21.0 and 21.4±0.2 degrees 2θ are most characteristic of this form. The X-ray powder diffraction peak positions and intensities exhibited by crystalline ibrutinib Form IX are listed in Table 7.

TABLE 7

| No. | Position [°2θ] | Relative Intensity [%] |
|---|---|---|
| 1 | 5.7 | 30 |
| 2 | 6.5 | 31 |
| 3 | 9.6 | 43 |
| 4 | 10.0 | 9 |
| 5 | 10.5 | 44 |
| 6 | 12.4 | 25 |
| 7 | 13.0 | 36 |
| 8 | 13.6 | 7 |
| 9 | 14.3 | 23 |
| 10 | 15.6 | 6 |
| 11 | 16.1 | 9 |
| 12 | 16.8 | 31 |
| 13 | 17.2 | 19 |
| 14 | 17.7 | 48 |
| 15 | 18.3 | 65 |
| 16 | 19.0 | 22 |
| 17 | 19.4 | 27 |
| 18 | 20.0 | 100 |
| 19 | 20.4 | 30 |
| 20 | 21.0 | 79 |
| 21 | 21.4 | 68 |
| 22 | 22.1 | 37 |
| 23 | 23.4 | 31 |
| 24 | 23.9 | 39 |
| 25 | 25.2 | 19 |
| 26 | 26.1 | 18 |
| 27 | 27.5 | 19 |
| 28 | 28.5 | 10 |
| 29 | 28.9 | 22 |
| 30 | 29.8 | 12 |
| 31 | 30.4 | 7 |
| 32 | 32.1 | 4 |

Figure 24:
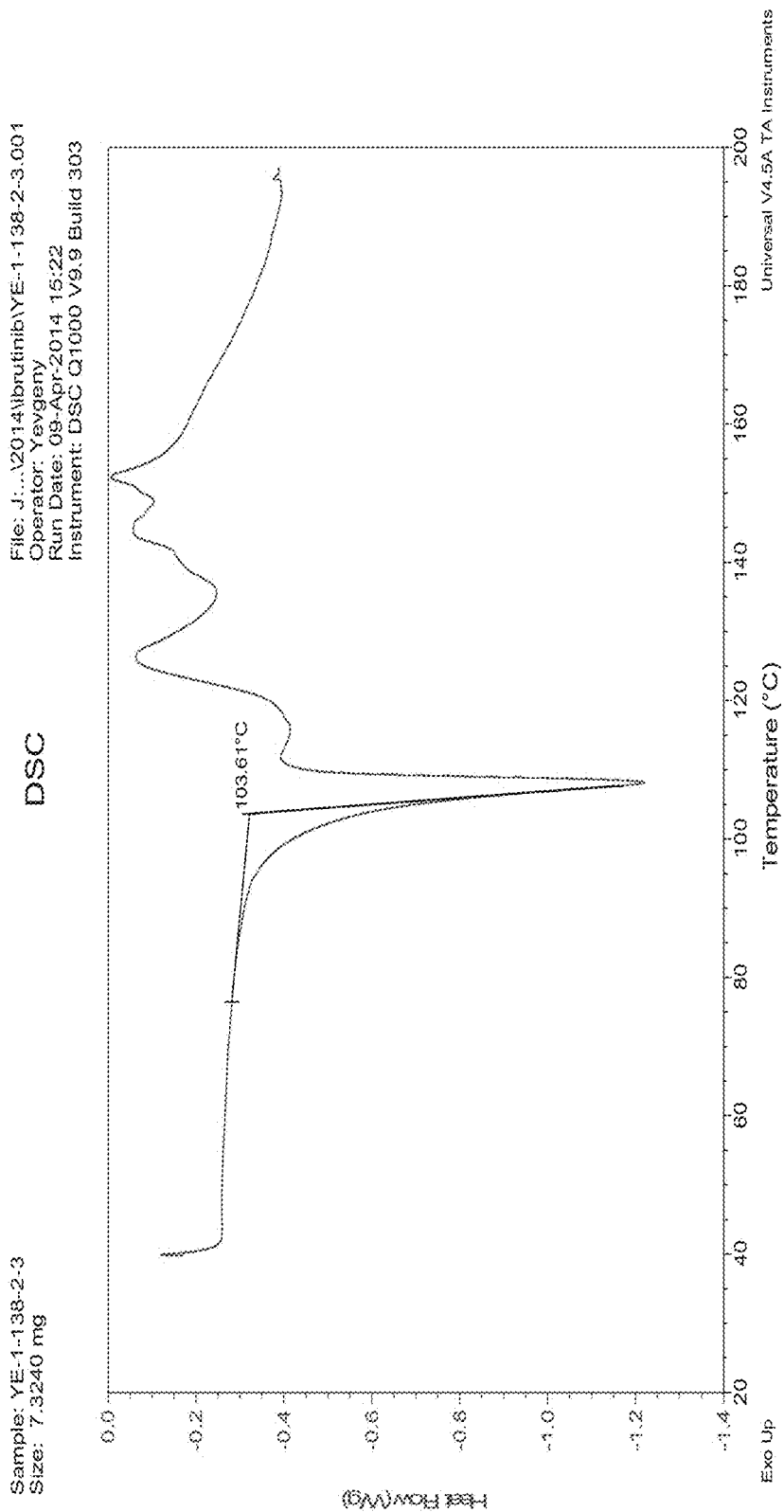
FIG. 24 depicts the DSC curve of crystalline ibrutinib Form IX.

The DSC curve of crystalline ibrutinib Form IX is depicted in FIG. 24 having peak onset at 103.6° C.

In one embodiment of the present invention, ibrutinib crystalline Form IX is an anisole solvate of ibrutinib.

In some embodiments, the present invention provides processes for preparing the crystalline ibrutinib polymorphs Form III, Form IV, Form V, Form VI, Form VII, Form VIII and Form IX.

The processes of the present invention for preparing ibrutinib Form III, Form IV, Form V, Form VI, Form VII, Form VIII and Form IX are selected from crystallization, slurrying in a solvent, vapor diffusion onto solids (VDS), vapor diffusion into solutions (VDL), thermal cycling (TCP), drying, exposing the material to accelerated aging conditions (AAC), grinding and combination of said methods.

One method of the present invention for producing irutinib Form III comprises vapor diffusion onto solids of amorphous ibrutinib. The process comprises the following steps:

exposing amorphous ibrutinib to vapors of 1,4-dioxane for a period of at least 1 day;

isolating the crystals, e.g., by filtration; and optionally drying the crystals to afford dry ibrutinib Form III.

In a preferred embodiment of the present invention, said exposing is carried out for two weeks.

One process of the present invention for preparing the crystalline ibrutinib Form IV, comprises:

dissolving ibrutinib in 1,2-dimethoxyethane, optionally with heating;

allowing the solution to cool or cooling the solution;

isolating the crystals, e.g., by filtration and, optionally, drying.

In one embodiment said heating is to reflux.

According to a specific embodiment of the present invention, a process for preparing ibrutinib crystalline Form IV in accordance with the present invention comprises the steps of dissolving ibrutinib in 1,2-dimethoxyethane under reflux and cooling to a temperature of 10° C. for about 5 hours to afford crystals of ibrutinib Form IV.

Another process of the present invention for preparing the crystalline ibrutinib Form IV, comprises:

slurrying ibrutinib in 1,2-dimethoxyethane, optionally with heating;

optionally cooling;

isolating the crystals and, optionally, drying.

In one embodiment said heating is to reflux.

A process of the present invention for preparing crystalline ibrutinib Form IV, comprises:

dissolving ibrutinib in 1,2-dimethoxyethane, optionally with heating;

subjecting the solution to cycles of heating and cooling (thermal cycling) until precipitation occurs;

isolating the obtained crystals, e.g., by filtration; and optionally drying the crystals.

In some embodiments of the present invention, the cycles of heating and cooling are from a temperature of 40° C. to a temperature of 5° C.

In some embodiments of the present invention, the heating and cooling cycles are carried out for at least 1 hour, preferable for 5 hours.

According to a specific embodiment of the present invention, a process for preparing ibrutinib crystalline Form IV in accordance with the present invention includes the steps of admixing ibrutinib with 1,2-dimethoxyethane and subjecting the mixture to about 8 cycles of heating and cooling from a temperature of 40° C. to a temperature of 5° C. until precipitation occurs, isolating the crystals, e.g. by filtration and optionally drying the crystals.

A process of the present invention for preparing ibrutinib Form V comprises:

mixing ibrutinib with methanol in a reaction vessel;

sonicating the mixture; and optionally separating the solid from the liquid.

In some embodiments the process for preparing ibrutinib Form V comprises several cycles of addition of methanol and sonication.

According to a specific embodiment of the present invention, a process for preparing ibrutinib crystalline Form V in accordance with the present invention includes the steps of placing ibrutinib Form A in a vessel, adding methanol, sonicating the mixture for at least 1 minute, optionally repeating the methanol addition and sonication until form V is obtained, and separating the crystals from the liquid e.g., by filtration or centrifugation.

A process of the present invention for preparing the crystalline ibrutinib Form VI comprises: placing wet ibrutinib Form IV in a climate chamber at a temperature of 40° C. and 75% relative humidity; exposing the material to a temperature of 40° C. and 75% relative humidity for a period of time sufficient to allow conversion to form VI; and optionally isolating the crystals of ibrutinib Form VI.

According to a specific embodiment of the present invention, a process for preparing ibrutinib crystalline Form VI in accordance with the present invention includes the steps of placing wet ibrutinib Form IV in a climate chamber at 40° C. and 75% relative humidity (accelerated aging conditions) for about 48 hours.

A process of the present invention for preparing crystalline ibrutinib Form VII, comprises the following steps:

dissolving ibrutinib in a first solvent;

exposing the solution to the vapors of a second solvent;

optionally isolating the obtained crystals, e.g., by filtration; and optionally drying the crystals to afford dry ibrutinib Form VII.

According to an embodiment of the present invention, said exposing the solution to the vapors of a second solvent is for a period of at least one day.

According to an embodiment of the present invention, the first solvent comprises anisole.

In some embodiments of the present invention, the second solvent is selected from acetone, cyclohexane, isooctane, petroleum ether, toluene, xylene and mixtures thereof. Preferably, the solvent is toluene.

According to a specific embodiment of the present invention, a process for preparing ibrutinib crystalline Form VII in accordance with the present invention includes the steps of dissolving ibrutinib (22 mg) in anisole to afford a saturated solution. Placing the open glass vessel, containing the solution of ibrutinib in anisole, in a closed vessel containing toluene and exposing the solution to toluene vapours for about two weeks to afford crystals of ibrutinib Form VII.

A process of the present invention for preparing the crystalline ibrutinib Form IX comprises:

inserting ibrutinib form VII into a ball mill;

milling the compound for sufficient time to allow conversion to ibrutinib form IX; and optionally isolating the crystals and drying.

Processes of the present invention for preparing amorphous ibrutinib are selected from removal of a solvent or solvents under reduced pressure, freeze-drying, spray-drying and milling.

A process of the present invention for preparing amorphous ibrutinib comprises:

dissolving ibrutinib in a solvent, optionally with heating; and distilling out the solvent optionally under reduced pressure.

In some embodiments of the present invention, the solvent is selected from 1,4-dioxane, ethyl acetate, methanol, tetrahydrofuran (THF), water and mixtures thereof.

Another process of the present invention for preparing amorphous ibrutinib, comprises:

dissolving ibrutinib in a first solvent, optionally with heating;

optionally adding a second solvent;

inserting the mixture into a spray-dryer and spray-drying; and isolating the formed solid and, optionally, drying the solid.

In some embodiments of the present invention, the first solvent is selected from dichloromethane, 1,4-dioxane, ethyl acetate, methanol, tetrahydrofuran (THF), water and mixtures thereof. Preferably, the solvent is dichloromethane.

In some embodiments of the present invention, the second solvent is selected form anisole, chlorobenzene, p-xylene and mixtures thereof. Preferably, the solvent is anisole.

According to a specific embodiment of the present invention, a process for preparing stable amorphous ibrutinib having slight hygroscopicity in accordance with the present invention comprises the steps of dissolving ibrutinib in dichloromethane at ambient temperature, introducing the solution into a spray dryer and carrying out spray-drying to obtain amorphous ibrutinib.

According to a preferred embodiment of the present invention, said stable amorphous ibrutinib produces same XRPD spectrum before and after two month of storage at room temperature in a closed vessel and it retains same chemical purity (according to HPLC) before and after one month of storage at room temperature in a closed vessel.

In one embodiment of the present invention a process for preparing amorphous ibrutinib comprises dissolving ibrutinib in a solvent or a mixture of solvents, optionally with heating, loading the solution onto a chromatographic column, eluting the ibrutinib from the column, optionally concentrating the eluting solution, spray drying the solution to give amorphous ibrutinib and optionally drying the amorphous product. In a preferred embodiment said amorphous ibrutinib is stable amorphous ibrutinib having slight hygroscopicity.

In one embodiment of the present invention said column is packed with silica.

In a specific embodiment of the present invention the ibrutinib loaded into said column comprises ibrutinib form VII or ibrutinib form IV.

In a specific embodiment of the present invention said eluting of the column comprises a first step of eluting with a first solvent or mixture of solvents and a second step of eluting with a second solvent or mixture of solvents. In a specific embodiment said first solvent is dichloromethane. In a specific embodiment said second mixture of solvents is a mixture of dichloromethane and methanol.

In an embodiment of the present invention amorphous ibrutinib obtained using the process comprising the use of a column is substantially free of impurities. In a specific embodiment of the present invention said impurities comprise anisole or dimethoxyethane.

In another embodiment of the present invention a process for preparing amorphous ibrutinib comprises dissolving ibrutinib in a solvent or a mixture of solvents, optionally with heating, mixing the solution with silica, filtering out the silica, optionally washing the silica, eluting the ibrutinib from the silica, optionally concentrating the eluting solution, spray drying the solution to give amorphous ibrutinib and optionally drying the amorphous product.

In a specific embodiment of the present invention said silica is washed in a first step with a first solvent or mixture of solvents and eluted in a second step with a second solvent or mixture of solvents. In a specific embodiment said first solvent is dichloromethane. In a specific embodiment said second mixture of solvents is a mixture of dichloromethane and methanol. In an embodiment of the present invention amorphous ibrutinib obtained using the process comprising mixing with silica is substantially free of impurities. In a specific embodiment of the present invention said impurities comprise anisole or dimethoxyethane. In a preferred embodiment said amorphous ibrutinib is stable amorphous ibrutinib having slight hygroscopicity.

Another process of the present invention for preparing the amorphous ibrutinib, comprises:

inserting ibrutinib into a ball mill;

milling the material for sufficient time to allow complete amorphization; and isolating the amorphous ibrutinib.

Another process of the present invention for preparing amorphous ibrutinib, comprises:

adding a solvent to solid ibrutinib to obtain a wet solid inserting the wet solid into a ball mill;

milling the material for sufficient time to allow complete amorphization; and isolating the amorphous ibrutinib.

Another process of the present invention for preparing amorphous ibrutinib, comprises:

adding a solvent to solid ibrutinib to obtain a wet solid;

inserting the wet solid into a ball mill;

milling the material;

carrying out a drying step;

repeating the milling and drying steps until the material is amorphous; and optionally isolating the amorphous ibrutinib.

In specific embodiments of the present invention said drying step is carried out under vacuum at elevated temperature.

According to a specific embodiment of the present invention, a process for preparing amorphous ibrutinib in accordance with the present invention comprises the steps of inserting ibrutinib Form A into a ball mill and milling for sufficient time to afford the amorphous product.

According to a specific embodiment of the present invention, a process for preparing amorphous ibrutinib in accordance with the present invention comprises the steps of adding ethyl acetate to ibrutinib form VIII. The wet solid thus obtained is inserted into a ball mill. Sequences of milling and drying are carried out to afford amorphous ibrutinib.

According to a specific embodiment of the present invention, a process for preparing amorphous ibrutinib in accordance with the present invention comprises the steps of adding ethyl acetate to ibrutinib form VIII. The wet solid thus obtained is inserted into a ball mill. Sequences of milling of at least 30 minutes and drying at 80 C under vacuum are carried out to afford amorphous ibrutinib.

A process of the present invention for preparing amorphous ibrutinib, comprises:

dissolving ibrutinib in a solvent or solvent mixture, optionally with heating;

optionally filtering the solution;

freezing the solution; and freeze-drying.

In some embodiments of the present invention, the solvent is selected from dichloromethane, 1,4-dioxane, ethyl acetate, methanol, tetrahydrofuran (THF), water and mixtures thereof. Preferably, a mixture of water and THF is employed.

According to a specific embodiment of the present invention, a process for preparing amorphous ibrutinib in accordance with the present invention includes the steps of dissolving ibrutinib in a solvent mixture of THF/Water (50:50), filtering the solution, freezing the solution and freeze-drying for a time sufficient to afford amorphous ibrutinib and optionally further drying the product.

The present invention provides pharmaceutical compositions comprising at least one of the forms of ibrutinib of the present invention, e.g., crystalline ibrutinib Form III, or crystalline ibrutinib Form IV, or crystalline ibrutinib Form V, or crystalline ibrutinib Form VI, or crystalline ibrutinib Form IX, or amorphous ibrutinib and at least one pharmaceutically acceptable excipient.

The present invention provides a process for preparing the pharmaceutical compositions comprising at least one of the crystalline forms or the amorphous forms of ibrutinib of the present invention and at least one pharmaceutically acceptable excipient.

Pharmaceutical compositions can be prepared by mixing at least one of the crystalline forms or the amorphous forms of ibrutinib of the present invention optionally with at least one additional active ingredient, with at least one pharmaceutically acceptable excipient selected from absorption accelerators, binders, bulking agents, carriers, diluents, disintegrants, fillers, lubricants, surface-active agents, wetting agents and the like.

The pharmaceutical compositions of the present invention can be administered, for example, as tablets, pills, powders, liquids, suspensions, emulsions, granules, capsules, suppositories, injection preparations (solutions and suspensions), and the like.

The present invention further provides methods of using the crystalline forms or amorphous forms of ibrutinib of the present invention in the treatment of diseases or conditions including diseases or conditions for which ibrutinib provides therapeutic benefit to a mammal having the disease or condition, such as, Mantle Cell Lymphoma (MCL) and Chronic Lymphocytic Leukemia (CLL) by administering to a subject in need thereof a therapeutically effective amount of said ibrutinib forms.

General process for obtaining amorphous ibrutinib comprising the use of a column: Ibrutinib form VII was dissolved in four volumes of dichloromethane. The solution was loaded onto a chromatographic column packed with silica (6-7.5 volumes of neutral silica; length/diameter ratio 4-5). The column was washed with 50 volumes of dichloromethane, then eluted with a mixture of dichloromethane:methanol (7-15% methanol content). The solution containing ibrutinib was concentrated to 10-15 volumes by distillation under reduced pressure. The concentrated solution was subjected to spray drying (exemplary conditions for spray drying are described e.g. in example 13).

EXAMPLES

The following examples further illustrate the invention but should not be construed as in any way limiting its scope.

General description of the equipment:

X-ray diffraction was measured using Panalytical X-ray diffractometer model X'Pert Pro. System description: CuK-Alpha1 wavelength=1.54060, voltage 45 kV, current 30 mA, diversion slit=0.25°, anti-scattering slit=0.5°;

Sample stage=Reflection-Transmission Spinner. Sample mode: Reflexion

Detector—X'Celerator;

Measurement parameters: Start Position [°2Th.]: 3; End Position [°2Th.]: 35; Step Size [°2Th.]: 0.004;

Scan Step Time [s]: standard 10.

Infrared spectra were run on Bruker Vertex 70, equipped with DTGS detector. All samples were run as KBr pellets. The current infra-red measurements are accurate to within 4 $cm^{-1}$.

Raman measurements were run on RAM-II module connected to Vertex 70. The samples used were tested without any sample preparation.

The Optical Microscope used was Olympus BX50 equipped with Zeiss Axiocam ERc5s digital camera (3.2 Mpixels). Imaging software: Zenlite 2011.

Differential scanning calorimetry (DSC) measurements were run on TA instruments model Q1000, with Universal software version 3.88. Samples were analyzed inside crimped 40 μl aluminum pans. Heating rate for all samples was 10° C./min.

Example 1

Ibrutinib (500 mg) was dissolved in a mixture of 5 ml each of anisole and acetone at a temperature of 80° C. in a 20 ml vial. The solvent mixture was evaporated under vacuum to afford a solid. The solid was dried in a vacuum oven at a temperature of 40° C. under vacuum (7.5 mBar) for 4.5 hours to afford crystals of ibrutinib Form VII.

Example 2

Ibrutinib (500 mg) was dissolved in a mixture of 5 ml each of anisole and cyclohehane at a temperature of 80° C. in a 20 ml vial. The solvent mixture was evaporated under vacuum to afford a solid. The solid was dried in a vacuum oven at a temperature of 40° C. under vacuum (7.5 mBar) for 4.5 hours to afford crystals of ibrutinib Form VII.

Example 3

Ibrutinib (5 g) was dissolved in 25 ml of anisole in a 100 ml three-neck round bottom flask, while heating to a temperature of about 77° C. The dissolving procedure was carried out in a controlled temperature oil bath having controlled stirring. After dissolution, cooling steps were carried out as follows:

| Stage No | Step description | Cooling rate or cooling time | Agitation speed |
|---|---|---|---|
| 1 | Cooling from 77° C. to a temperature above 25° C. | 10° C./hour | 300 rpm |
| 2 | Cooling to 25° | 120 minutes | 300 rpm |
| 3 | Cooling from 25° C. to 5° C. | 10° C./hour | 200 rpm |
| 4 | 5° C. | overnight | 200 rpm |

After cooling, the liquid was removed by filtration. The obtained solid was kept in the filter for further 15 minutes. The solid was dried in a vacuum oven at a temperature of 40° C. under vacuum (7.5 mBar) for 4.5 hours to afford crystals of ibrutinib Form VII.

Example 4

Ibrutinib (500 mg) was admixed with 5 ml of anisole at a temperature of 50° C. in a 20 ml vial to afford a solution. 10 ml of petroleum ether (b.p. 60-80° C.) was added drop-wise to the mixture. A solid formed. The solid was collected by filtration. The obtained wet material was dried in a vacuum oven at 80° C. under vacuum (7.5 mBar) for 3.5 hours to afford crystals of ibrutinib Form VII.

Example 5

Ibrutinib (500 mg) was admixed with 7.5 ml of anisole at a temperature of 50° C. in a 20 ml vial to afford a solution. 12 ml of isooctane was added drop-wise to the mixture. A solid formed. The solid was collected by filtration. The obtained wet material was dried in a vacuum oven at 80° C. under vacuum (7.5 mBar) for 3.5 hours to afford crystals of ibrutinib Form VII.

Example 6

Ibrutinib (500 mg) was admixed with 7.5 ml of anisole at a temperature of 50° C. in a 20 ml vial to afford a solution. 12 ml of xylene was added drop-wise to the mixture. A solid formed. The solid was collected by filtration. The obtained wet material was dried in a vacuum oven at 80° C. under vacuum (7.5 mBar) for 3.5 hours to afford crystals of ibrutinib Form VII.

Example 7

Ibrutinib (500 mg) was mixed with 4 ml of anisole at a temperature of 60° C. in a 20 ml vial. The mixture was slowly cooled to 5° C. overnight and seeded with crystals of crystalline ibrutinib Form VII. The thus obtained solid was collected by filtration. The obtained wet material was dried in a vacuum oven at 80° C. under vacuum (7.5 mBar) for 3.5 hours to afford crystals of ibrutinib Form VII.

Example 8

Ibrutinib (5 g) was dissolved in 25 ml of chlorobenzene with heating to a temperature of 80° C. in a 100 ml three-neck round bottom flask. The dissolving procedure was carried out in a controlled temperature oil bath with controlled stirring. After dissolution, the cooling steps were carried out as follows:

| Stage No | Step description | Cooling rate or cooling time | Agitation speed |
|---|---|---|---|
| 1 | Cooling from 80° C. to a temperature above 25° C. | 10° C./hour | 300 rpm |
| 2 | Cooling to 25° | 120 minute | 300 rpm |
| 3 | Cooling from 25° C. to 5° C. | 10° C./hour | 200 rpm |
| 4 | 5° C. | overnight | 200 rpm |

After cooling, the liquid was removed by filtration. The obtained solid was kept in the filter for additional period of 15 minutes. The solid was dried in a vacuum oven at 40° C. under vacuum (7.5 mBar) for 4.5 hours to afford crystals of ibrutinib Form VIII.

Example 9

Ibrutinib (500 mg) was dissolved in a mixture of 5 ml each of chlorobenzene and toluene at a temperature of 50° C. in a 20 ml vial. The solvent mixture was evaporated under vacuum to afford a solid. The solid was dried in a vacuum oven at a temperature of 40° C. under vacuum (7.5 mBar) for 4.5 hours to afford crystals of ibrutinib Form VIII.

Example 10

Ibrutinib (1 g) was dissolved in 15 ml of chlorobenzene with heating to 65° C. in a 20 ml vial. After dissolution, the vial was sealed and cooled to ambient temperature followed by cooling to 4° C. overnight. After cooling, the liquid was removed by filtration. The obtained solid was kept in the filter for an additional period of 15 minutes (0.98 g, 98% yield). The solid was dried in a vacuum oven at a temperature of 40° C. under vacuum (7.5 mBar) for 5 hours to afford crystals of ibrutinib Form VIII.

Example 11

Ibrutinib form A (400 mg) was slurried overnight in 1 ml of anisole in a 20 ml vial with heating to 50° C. After cooling, the solvent was removed by filtration. The obtained solid was dried in a vacuum oven at a temperature of 80° C. under vacuum for 3 hours to afford crystals of ibrutinib Form VII.

Example 12

Ibrutinib Form A (2.1 g) was inserted into a ball mill equipped with capsule of 50 mm diameter and one ball. Both the capsule and the ball were made of stainless steel. The milling was conducted at 30 Hz frequency. Amorphous ibrutinib was recovered after about 36 minutes of milling.

Example 13

Ethyl acetate (1 mL) was added to ibrutinib form VIII (3 g). A wet solid was obtained and the wet solid was inserted into a Retsch MM400 ball mill within a capsule of 50 mm diameter and a ball. Both the capsule and the ball were made of stainless steel. Sequences of milling and drying were carried out; 2×30 minutes of milling and 2×1 hour of drying at 80° C. under vacuum followed by additional 3.5 hours of dryings at 80° C. under vacuum to afford amorphous ibrutinib. The content of residual chlorobenzene (according to GC) was: 450 ppm.

Example 14

Ibrutinib Form VII (11.1 g) was dissolved in dichloromethane at ambient temperature. The solution was introduced into Buchi spray dryer model B-290. The solution volume used was 220 ml. The parameters of the spray drying that were used are listed in the following Table 8:

TABLE 8

| Concentration, % | $T_{in}$, ° C. | $T_{out}$, ° C. | Pump speed, % | $N_2$ flow | Aspirator, % | Nozzle cleaner |
|---|---|---|---|---|---|---|
| 5 | 60 | 46 | 5 | 45 | 80 | 0 |

The obtained dried amorphous material had residual dichloromethane content of 1300 ppm according to GC.

Example 15

Ibrutinib form VII was dissolved in four volumes of dichloromethane. The solution was loaded onto a chromatographic column packed with silica (6-7.5 volumes of neutral silica; length/diameter ratio 4-5). The column was washed with 50 volumes of dichloromethane, then eluted with a mixture of dichloromethane: methanol (7-15% methanol content). The solution containing ibrutinib was concentrated to 10-15 volumes by distillation under reduced pressure. The concentrated solution was subjected to spray drying.

Example 16

Ibrutinib Form A (8.9 g) was dissolved in dichloromethane at room temperature. Anisole was added to the solution (1 mL). The solution was introduced into Buchi spray dryer model B-290. The solution volume used was 220 mL. The parameters of the spray drying that were used are listed in the following Table 9:

TABLE 9

| Concentration, % | $T_{in}$, °C. | $T_{out}$, °C. | Pump speed, % | $N_2$ flow | Aspirator, % | Nozzle cleaner |
|---|---|---|---|---|---|---|
| 5 | 80 | 60 | 5 | 45 | 100 | 0 |

The yield of the obtained amorphous material was 61%. Additional drying in vacuum oven at 80° C. under vacuum for 2.5 hours was conducted. After the additional drying, the anisole content (by GC) was less than 300 ppm. No dichloromethane residual content was detected after the additional drying.

Example 17

Hygroscopicity test was performed on amorphous ibrutinib that was obtained by spray-drying as demonstrated in Example 4. The hygroscopicity test was carried out according to the European Pharmacopoeia, 5.11 Characters Section in Monographs at ambient temperature (about 25° C.) on substance "as is".

Desiccator with saturated ammonium chloride solution was prepared as follows: to a 100 mL of water was added accurately weighed 46.3 g of ammonium chloride under mixing. The solubility of ammonium chloride in water at ambient temperature is about 41.4 g/100 mL water at 30° C. An amount of amorphous ibrutinib was placed in a glass weighing vessel with stopper ($m_1$) and weighed ($m_2$). The un-stoppered vessel was placed in a desiccator containing a saturated solution of ammonium chloride (80±2% relative humidity) at 25° C. for 24 hours. The weighing vessel was stoppered and weighed ($m_3$). The percentage increase in mass was calculated according to the following formula:

$$\frac{m_3 - m_2}{m_2 - m_1} \times 100$$

The following Table 10 includes the standard defined hygroscopicity values according to the European Pharmacopoeia, 5.11 Characters Section in Monographs:

TABLE 10

| Definition of degree of hygroscopicity | Hygroscopicity value |
|---|---|
| Deliquescent | Sufficient water is absorbed to form a liquid |
| Very hygroscopic | Increase in mass is equal to or greater than 15% |
| Hygroscopic | Increase in mass is less than 15% and equal to or greater than 2% |
| Slightly hygroscopic | Increase in mass is less than 2% and equal to or greater than 0.2% |

Table 11 below includes the results of the hygroscopicity test as follows:

TABLE 11

| $m_1$, g | $m_2$ g | $m_3$, g | Increase in mass | |
|---|---|---|---|---|
| | | | g | % |
| 49.78852 | 50.65569 | 50.66646 | 0.01077 | 1.24% |

The increase in mass was equal to 1.24%, which renders the tested material as slightly hygroscopic.

Example 18

A solution of ibrutinib (400 mg) in a solvent mixture of THF/Water (50:50) was prepared having concentration of 80 mg/mL. The solution was filtered using 0.45 μm filter to remove un-soluble material. The solution was placed in liquid nitrogen to afford freezing and inserted into a Labconco FreeZone 2.5L freeze-dryer for 24 hours. The material was further dried at 60° C. and 5 mbar for 24 hours to yield amorphous ibrutinib.

Example 19

Ibrutinib (500 mg) was dissolved in a mixture of 5 mL each of anisole and acetone at a temperature of 80° C. in a 20 mL vial. The solvent mixture was evaporated under vacuum to afford a solid. The solid was dried in a vacuum oven at a temperature of 40° C. under vacuum (7.5 mBar) for 4.5 hours to afford crystals of ibrutinib Form VII.

Table 12 below includes crystal data and structure refinement of crystalline ibrutinib Form VII

TABLE 12

| Sample identification | Ibrutinib Form VII |
|---|---|
| T (K) | 296 (2) |
| λ [Å] | 0.71073 |
| Crystal system | Triclinic |
| Space group | P1 |
| Unit cell dimensions | |
| a [Å] | 10.1772 (9) |
| b [Å] | 10.3719 (9) |
| c [Å] | 14.0393 (12) |
| α (°) | 93.9802 (15) |
| β (°) | 100.9442 (15) |
| γ (°) | 116.2116 (13) |
| V [Å$^3$] | 1285.46 (19) |
| Z | 2 |
| $D_c$ [g/cm$^3$] | 1.278 |
| μ [mm$^{-1}$] | 0.082 |
| F(000) | 522 |
| Crystal size [mm$^3$] | 0.40 × 0.25 × 0.25 |
| θ range for data collection [°] | 2.68 to 32.64° |
| Reflections collected | 14563 |
| Independent reflections | 9277 [R(int) = 0.0257] |
| Completeness to θ = 32.64 [%] | 98.4 |
| Max. and Min. transmission | 0.9791 and 0.9669 |

TABLE 12-continued

| Sample identification | Ibrutinib Form VII |
|---|---|
| Data/restrains/parameters | 9277/3/671 |
| Goodness-of-fit on $F^2$ | 1.038 |
| Final R indices [I > 2σ(I)] | R1 = 0.0620, wR2 = 0.1544 |
| R indices (all data) | R1 = 0.0905, wR2 = 0.1797 |

Example 20

Ibrutinib (22 mg) was dissolved in 700 μL of anisole in a 1.8 mL vial to afford a saturated solution. The open vial, containing the solution of ibrutinib in anisole, was placed in a 40 mL closed vial containing 2 mL of toluene. The saturated solution was exposed to vapor diffusion into the solution for two weeks to afford crystals of ibrutinib Form VII, which were dried in a vacuum oven at elevated temperature.

Example 21

Ibrutinib (5 g) was dissolved in chlorobenzene (25 mL) with heating to a temperature of 80° C. in a 100 ml three-neck round bottom flask. The dissolving procedure was carried out in a controlled temperature oil bath with controlled stirring. After dissolution, cooling steps as detailed in Table 13 below were carried out as follows:

TABLE 13

| Stage No | Step description | Cooling rate or cooling time | Agitation speed |
|---|---|---|---|
| 1 | Cooling from 80° C. to a temperature above 25° C. | 10° C./hour | 300 rpm |
| 2 | Cooling to 25° | 120 minute | 300 rpm |
| 3 | Cooling from 25° C. to 5° C. | 10° C./hour | 200 rpm |
| 4 | 5° C. | overnight | 200 rpm |

After cooling, the liquid was removed by filtration. The obtained solid was kept in the filter for additional period of 15 minutes. The solid was dried in a vacuum oven at 40° C. under vacuum (7.5 mBar) for 4.5 hours to afford crystals of ibrutinib Form VIII.

Example 22

Amorphous ibrutinib (19.9 mg), prepared by freeze-drying, was placed in a 1.8 mL vial. The vial containing the amorphous ibrutinib was left open in a 40 mL vial containing 1,4-dioxane (2 mL). The material was exposed to the vapors of 1,4-dioxane in the vial for a period of about two weeks. The solid was collected by filtration to afford crystals of ibrutinib Form III having purity of 99.6%, according to HPLC.

Example 23

A solution of ibrutinib Form A (23 μg) in 1,2-dimethoxyethane (300 μL) was prepared in a 1.8 mL vial and subjected to 8 cycles of heating and cooling from 40° C. to 5° C. for 5 hours until precipitation occurred. The obtained wet solid was collected by filtration to afford crystals of ibrutinib Form IV having purity of 99.2%, according to HPLC.

Example 24

Ibrutinib Form A (1 g) was dissolved in 1,2-dimethoxyethane (5 mL) under reflux at 85° C. and then cooled to 10° C. for 5 hours. The obtained wet solid was collected by filtration and dried under vacuum at 40° C. for 16 hours to afford crystals of ibrutinib Form IV.

Example 25

Ibrutinib Form A (22 mg) was placed in a 1.8 mL vial. 4×100 μL methanol aliquots were added and in between every solvent addition the vial was sonicated for a period of 1 minute (the total solvent volume was 400 μL). Then, the solid was separated from the liquid by centrifugation. The solid was collected to afford wet crystals of ibrutinib Form V.

Example 26

A vial containing ibrutinib Form IV, obtained as described in Example 11, was placed in a climate chamber at 40° C. and 75% relative humidity (RH) for 48 hours. After the exposure, the solid was collected to afford crystals of ibrutinib Form VI having purity of 99.9%, according to HPLC.

Example 27

Ibrutinib Form VII was produced as described herein in Example 8. Ibrutinib Form VII (4.5 g) was inserted into a Retsch MM400 ball mill with a capsule of 50 mm diameter and a ball, both made of stainless steel. The milling was conducted at 30 Hz frequency to afford ibrutinib Form IX after about 37 minutes of milling. The crystals were collected and dried.

Example 28

Ibrutinib form VII (5 g) was wetted with about 1.5 mL of acetone and inserted into a Retsch MM400 ball mill equipped with a capsule of 50 mm diameter and ball both made of stainless steel. The milling was conducted at 30 Hz frequency to afford ibrutinib Form IX after about 30 minutes of milling. The solid was collected and dried. The same procedure was carried out with ethanol to yield ibrutinin Form IX as well.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. Crystalline ibrutinib Form VII characterized by an X-ray powder diffraction pattern exhibiting strong diffraction peaks at 6.5, 13.0, 17.7, 18.3, 20.0, 21.0, 21.5, and 23.9±0.2 degrees 2θ.

2. The crystalline ibrutinib Form VII of claim 1 further characterized by an infrared spectrum exhibiting characteristic absorption bands at 3433, 1587, 1491, 1437, 1238, 986, 862, and 692 cm$^{-1}$.

3. The crystalline solid ibrutinib Form VII of claim 1 further characterized by DSC curve exhibiting peak onset at 116.7° C.

4. A pharmaceutical composition comprising crystalline ibrutinib Form VII and one or more pharmaceutically acceptable additives or excipients.

5. A process for preparing crystalline ibrutinib polymorph VII, the process comprising:
   dissolving or slurrying ibrutinib in anisole or in a mixture of anisole with another solvent or anti-solvent; optionally heating;
   optionally adding an anti-solvent;
   optionally cooling;
   optionally seeding with crystalline ibrutinib Form VII; and
   isolating the solid and, optionally, drying the solid.

6. The process of claim 5, wherein said other solvent or anti-solvent is selected from acetone, cyclohexane, petroleum ether, isooctane, and xylene.

7. The process of claim 5, wherein said crystalline ibrutinib Form VII has a purity of at least 98%.

8. The process of claim 5, wherein the mixture is heated to a temperature of between 40° C. and 90° C.

9. The process of claim 5, wherein cooling is carried out gradually.

10. A process for preparing ibrutinib Form VII, comprising:
    dissolving ibrutinib in a first solvent;
    exposing the solution to the vapors of a second solvent for a period of at least one day to produce crystals;
    isolating the crystals; and
    optionally drying the crystals to afford dry ibrutinib Form VII.

11. The process of claim 10, wherein the first solvent comprises anisole.

12. The process of claim 10, wherein the second solvent is selected from acetone, cyclohexane, isooctane, petroleum ether, toluene, xylene and mixtures thereof.

13. A method for treating mantle cell lymphoma and chronic lymphoid leukemia comprising administering to a subject in need a therapeutically effective dose of ibrutinib Form VII.

* * * * *